United States Patent
Brown et al.

[11] Patent Number: 5,593,874
[45] Date of Patent: Jan. 14, 1997

[54] ENHANCED EXPRESSION IN PLANTS

[75] Inventors: Sherri M. Brown, Chesterfield; Colleen G. Santino, St. Louis, both of Mo.

[73] Assignee: Monsanto Company, St. Louis, Mo.

[21] Appl. No.: 333,665

[22] Filed: Nov. 3, 1994

Related U.S. Application Data

[63] Continuation of Ser. No. 181,364, Nov. 13, 1994, Pat. No. 5,424,412, which is a continuation of Ser. No. 855,857, Mar. 19, 1992, abandoned.

[51] Int. Cl.$^6$ .............................. A01H 1/04; C12N 15/00
[52] U.S. Cl. .................. 435/172.3; 435/69.1; 800/205; 800/DIG. 55; 800/DIG. 56; 800/ DIG. 57; 800/DIG. 58; 935/35; 536/24.1
[58] Field of Search ................ 800/205, DIG. 55, 800/DIG. 56, DIG. 57, DIG. 58; 536/23.1, 24.1; 435/172.3, 69.1, 70.1, 320.1; 935/35

[56] References Cited

PUBLICATIONS

Winter et al., The inhibition of petunia hsp70 mRNA processing during CdCl2 stress. Mol. Gen. Genet. 211:315–319 (1988).

della–Cioppa et al, Translocation of the precursor of 5–enolpyruvyl–shikimate–3–phosphate synthase into chloroplasts of higher plants in vitro. Proc. Natl. Acad. Sci. USA 83:6873–3877 (1986).

Sheehy et al., Isolation, sequence, and expression in *Escheerichia coli* of the Pseudomonas sp. strain, ACP gene encoding 1–aminocyclopropane–1–carboxylate deaminase. J of Bacteriology 5160–5265 (1991).

McPherson et al., Characterization of the coleopteran–specific protein gene of *Bacillus thuringiensis* var. tenebionis. Bio/Technology 6:61–66 (1988).

Leung et al., Cloning and expression of the *Excherichia coli* glgC gene from a mutant containing an ADPglucose pyrophosphorylase with altered allosteric properties. J of Bacteriology 82–88 (1986).

Rhodes et al., Genetically transformed maize plants from protoplasts. Science 240:204–207 (1988).

Shimamoto et al., Fertile transgenic rice plants regenerated from transformed protoplasts. Nature 338:274–276 (1989).

Wang et al., Transient expression of foreign genes in rice, wheat and soybean cells following particle bombardment. Plant Mol. Bio. 11:433–439 (1988).

Vasil et al., Regeneration of plants from embryogenic suspension culture protoplasts of wheat (*Triticum aestivum* L.). Bio/Technology 9:429–434 (1990).

Cuozzo et al., Viral protection in transgenic tobacco plants expressing the cucumber mosaic virus coat protein or its antisense RNA. Bio/Technology 6:549–557 (1988).

Callis et al., Introns increase gene expression in cultured maize cells. Genes & Development 1:1183–1200 (1987) Cold Spring Harbor Lab.

Rochester et al., The structure and expression of maize genes encoding the major heat shock protein, hsp70. EMBO J. 5(3):451–458 (1986).

Gelvin, S. B. (1987) Plant Mol Biol 8:355–359.

*Primary Examiner*—David T. Fox
*Assistant Examiner*—Elizabeth F. McElwain
*Attorney, Agent, or Firm*—Dennis R. Hoerner, Jr.; Grace L. Bonner

[57] ABSTRACT

This invention provides HSP70 introns that when present in a non-translated leader of a chimeric gene enhance expression in plants.

23 Claims, 28 Drawing Sheets

```
  1  AGATCTACCG TCTTCGGTAC GCGCTCACTC CGCCCTCTGC CTTTGTTACT
 51  GCCACGTTTC TCTGAATGCT CTCTTGTGTG GTGATTGCTG AGAGTGGTTT
101  AGCTGGATCT AGAATTACAC TCTGAAATCG TGTTCTGCCT GTGCTGATTA
151  CTTGCCGTCC TTTGTAGCAG CAAAATATAG GACATGGTA GTACGAAACG
201  AAGATAGAAC CTACACAGCA ATACGAGAAA TGTGTAATTT GGTGCTTAGC
251  GGTATTTATT TAAGCACATG TTGGTGTTAT AGGGCACTTG GATTCAGAAG
301  TTTGCTGTTA ATTTAGGCAC AGGCTTCATA CTACATGGGT CAATAGTATA
351  GGGATTCATA TTATAGGCGA TACTATAATA ATTTGTTCGT CTGCAGAGCT
401  TATTATTTGC CAAAATTAGA TATTCCTATT CTGTTTTTGT TTGTGTGCTG
451  TTAAATTGTT AACGCCTGAA GGAATAAATA TAAATGACGA AATTTTGATG
501  TTTATCTCTG CTCCTTTATT GTGACCATAA GTCAAGATCA GATGCACTTG
551  TTTTAAATAT TGTTGTCTGA AGAAATAAGT ACTGACAGTA TTTTGATGCA
601  TTGATCTGCT TGTTTGTTGT AACAAAATTT AAAAATAAAG AGTTTCCTTT
651  TTGTTGCTCT CCTTACCTCC TGATGGTATC TAGTATCTAC CAACTGACAC
701  TATATTGCTT CTCTTTACAT ACGTATCTTG CTCGATGCCT TCTCCCTAGT
751  GTTGACCAGT GTTACTCACA TAGTCTTTGC TCATTTCATT GTAATGCAGA
801  TACCAAGCGG CCATGG
```

FIG. 1

```
  1  AGATCTACCG TCTTCGGTAC GCGCTCACTC CGCCCTCTGC CTTTGTTACT
 51  GCCACGTTTC TCTGAATGTG ATCTGCTTGT TTGTTGTAAC AAAATTTAAA
101  AATAAAGAGT TTCCTTTTTG TTGCTCTCCT TACCTCCTGA TGGTATCTAG
151  TATCTACCAA CTGACACTAT ATTGCTTCTC TTTACATACG TATCTTGCTC
201  GATGCCTTCT CCCTAGTGTT GACCAGTGTT ACTCACATAG TCTTTGCTCA
251  TTTCATTGTA ATGCAGATAC CAAGCGGCCA TGG
```

```
  1 AGATCTACCG TCTTCGGTAC GCGCTCACTC CGCCCTCTGC CTTTGTTACT
 51 GCCACGTTTC TCTGAATGGT ATCTTGCTCG ATGCCTTCTC CCTAGTGTTG
101 ACCAGTGTTA CTCACATAGT CTTTGCTCAT TTCATTGTAA TGCAGATACC
151 AAGCGGCCAT GG
```

ENHANCED EXPRESSION IN PLANTS

This is a Continuation of application Ser. No. 08/181,364, filed Jan. 13, 1994, now U.S. Pat. No. 5,424,412, which is a Continuation of application Ser. No. 07/855,857, filed Mar. 19, 1992, now abandoned.

This invention relates to recombinant expression systems, particularly to plant expression systems for expressing greater quantities of proteins in plants.

BACKGROUND OF THE INVENTION

Recombinant genes for producing proteins in plants comprise in sequence a promoter which functions in plants, a structural gene encoding the target protein, and a nontranslated region that functions in plants to cause the addition of polyadenylated nucleotides to the RNA sequence. Much scientific effort has been directed to improve these recombinant plant genes to express larger amounts of the target protein.

One advantage of higher levels of expression is that fewer numbers of transgenic plants need to be produced and screened to recover plants producing sufficient quantities of the target protein to be agronomically significant. High level expression leads to plants exhibiting commercially important phenotypical properties.

Improved recombinant plant genes have been found by use of more potent promoters, such as promoters from plant viruses. Further improvement in expression has been obtained in gene constructs by placing enhancer sequences 5' the promoter. Still further improvement has been achieved, especially in monocot plants by gene constructs having introns in the non-translated leader positioned between the promoter and the structural gene coding sequence. For example, Callis et al. (1987) *Genes and Development*, Vol. 1, pp. 1183–1200, reported that the presence of alcohol dehydrogenase-1 (Adh-1) introns or Bronze-1 introns resulted in higher levels of expression. Dietrich et al. (1987) *J. Cell .Biol.*, 105, p. 67, reported that the 5' untranslated leader length was important for gene expression in protoplast. Mascarenkas et al. (1990) *Plant Mol. Biol.*, Vol. 15, pp. 913–920, reported a 12-fold and 20-fold enhancement of CAT expression by use of the Adh-1 intron. Vasil et al. (1989) *Plant Physiol.*, 91, pp. 1575–1579, reported that the Shrunken-1 (Sh-1) intron gave about 10 times higher expression than constructs containing the Adh-1 intron. Silva et al. (1987) *J. Cell Biol.*, 105, p. 245, reported a study of the effect of the untranslated region of the 18 Kd heat shock protein (HSP18) gene on expression of CAT. Semrau et al. (1989) *J. Cell Biol.*, 109, p. 39A, and Mettler et al., N.A.T.O. Advanced Studies Institute on Molecular Biology, Elmer, Bavaria (May 1990) reported that the 140 bp intron of the 82 Kd heat shock protein (HSP82) enhanced expression in maize protoplasts.

The search for even more improved recombinant plant genes continues for the reasons discussed above.

SUMMARY OF THE INVENTION

This invention is for an improved method for the expression of a chimeric plant gene in plants, particularly to achieve higher expression in monocot plants. The improvement of the invention comprises expressing a chimeric plant gene with an intron derived from the 70 Kd maize heat shock protein (HSP70) selected from the group consisting essentially of SEQ ID NO:1, SEQ ID NO:2 and SEQ ID NO:3 in the non-translated leader positioned 3' from the gene promoter and 5' from the structural DNA sequencing encoding a protein.

One embodiment of the invention is a recombinant, double stranded DNA molecule comprising in sequence:
(a) a promoter that functions in plant cells to cause the production of an RNA sequence;
(b) a non-translated leader DNA sequence comprising an intron selected from the group consisting essentially of SEQ ID NO:1, SEQ ID NO:2 and SEQ ID NO:3;
(c) a structural DNA sequence that causes the production of an RNA sequence that encodes a protein; and
(d) a 3' non-translated sequence that functions in plant cells to cause the addition of polyadenylated nucleotides to the 3' end of the RNA sequence, the intron being heterologous with respect to the promoter.

Another embodiment of the invention is an isolated DNA sequence consisting essentially of the nucleotides shown in SEQ ID NO:1.

Another embodiment of the invention is a synthetic DNA sequence selected from the group consisting essentially of the nucleotides shown in SEQ ID NO:2 and nucleotides shown in SEQ ID NO:3.

Another embodiment of the invention is transgenic plants, particularly monocot plants, comprising the chimeric plant genes described above. The resultant transgenic plants are capable of expressing a foreign gene which has been inserted into the chromosome of the plant cell.

The invention provides chimeric plant genes that, when expressed in a transgenic plant, provide greater quantities of the desired protein encoded by the structural coding sequence in the chimeric gene of the invention. The high protein levels impart important agronomic properties to the plant depending on which protein is present. For example, expression of a *Bacillus thuringiensis* crystal toxin protein protects the transgenic plant from insect attack. Expression of a plant virus coat protein protects the transgenic plant from plant viral infections. Expression of a glyphosate tolerant gene protects the transgenic plant from the herbicidal action of glyphosate herbicide.

BRIEF DESCRIPTION OF THE DRAWINGS

FIG. 1 illustrates the DNA sequence of the intron from the 70 Kd maize heat shock protein, SEQ ID NO:1.

Figure 2:
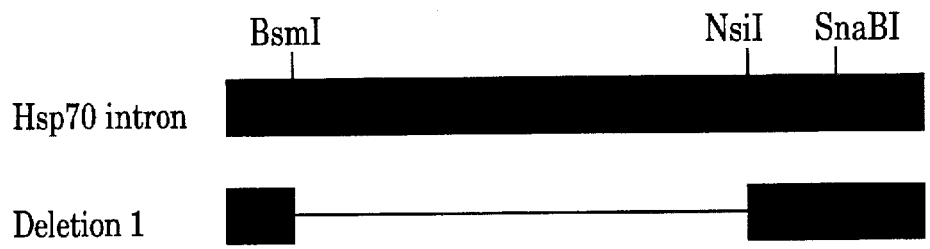
FIG. 2 illustrates a truncated DNA sequence with internal deletions of the intron from the 70 Kd maize heat shock protein, SEQ ID NO:2.

The intron of the chimeric gene of this invention was derived using the polymerase chain reaction (PCR) from the 70 Kd maize heat shock protein (HSP70) in pMON9502 described by Rochester et al. (1986) *Embo. J.*, 5:451–458. The intron sequence disclosed herein (SEQ ID NO:1) contains 773 base pair HSP70 intron with 10 base pairs of flanking 5' exon sequence and 11 base pairs of flanking 3' exon sequence. The primers used to isolate the intron are designed such that the PCR product contains a 6 base pair BglII site at the 5' end and a 6 base pair NcoI site at the 3' end.

Chimeric genes are constructed by inserting the intron into BglII and NcoI sites in the 5' non-translated leader of an expression vector comprising a plant promoter, a scorable marker coding sequence, and a polyadenylated coding sequence. The expression vectors are constructed with the appropriate restriction sites which permit the insertion of a structural DNA sequence encoding the desired protein. Conventional cloning and screening procedures are used throughout unless otherwise noted.

A gene of this invention containing the HSP70 intron can be inserted into a suitable plant transformation vector for transformation into the desired plant species. Suitable plant transformation vectors include those derived from a Ti plasmid of *Agrobacterium tumefaciens*. A plant transformation vector preferably includes all of the necessary elements needed for transformation of plants or plant cells. Typical plant transformation vectors comprise selectable marker genes, one or both of the T-DNA borders, cloning sites, appropriate bacterial genes to facilitate identification of transconjugates, broad host-range replication and mobilization functions and other elements as desired.

Transformation of plant cells may be effected by delivery of a transformation vector or of free DNA by use of a particle gun which comprises directing high velocity micro-projectiles coated with the vector or DNA into plant tissue. Selection of transformed plant cells and regeneration into whole plants may be carried out using conventional procedures. Other transformation techniques capable of inserting DNA into plant cells may be used, such as electroporation or chemicals that increase free DNA uptake.

The HSP70 intron cDNA sequence is inserted into a plant transformation vector as a gene capable of being expressed in a plant. For the purposes of this invention, a "gene" is defined as an element or combination of elements that are capable of being expressed in a plant, either alone or in combination with other elements. Such a gene generally comprises, in the following order, a promoter that functions in plant cells, a 5' non-translated leader sequence, a DNA sequence coding for the desired protein, and a 3' non-translated region that functions in plants to cause the addition of polyadenylated ribonucleotides to the 3' end of the mRNA transcript. In this definition, each above described element is operationally coupled to the adjacent element. A plant gene comprising the above elements can be inserted by known, standard recombinant DNA methods into a plant transformation vector and other elements added to the vector when necessary. A plant transformation vector can be prepared that has all of the necessary elements for plant expression except that the desired DNA region encoding a protein or portion thereof, which DNA coding region can readily be added to the vector by known methods. Generally, an intron of this invention is inserted into the 5' non-translated leader sequence.

Any promoter that is known or found to cause transcription of DNA in plant cells can be used in the present invention. The amount of enhancement of expression by use of the introns of this invention may vary from promoter to promoter as has been observed by use of other introns. See Callis et al., supra, and Mascanenkas et al., supra. Suitable promoters can be obtained from a variety of sources such as plants or plant DNA viruses and include, but are not necessarily limited to, promoters isolated from the caulimovirus group, such as the cauliflower mosaic virus 19S and 35S (CaMV19S and CaMV35S) transcript promoters or the figwort mosaic virus full-length transcript promoter (FMV35S). The FMV35S promoter causes a high level of uniform expression of a protein coding region coupled thereto in most plant tissues. Other useful promoters include the enhanced CaMV35S promoter (eCaMV35S) as described by Kat et al. (1987) *Science* 236:1299–1302, and the small subunit promoter of ribulose 1,5-bisphosphate carboxylase oxygenase (RUBISCO).

Examples of other suitable promoters are rice actin promoter; cyclophilin promoter; ubiquitin promoter; ADH1 promoter, Callis et al., supra.; Class I patatin promoter, Bevan et al. (1986) *Nucleic Acids Res.* 14 (11), 4675–4638;

ADP glucose pyrophosphorylase promoter; β-conglycinin promoter, Tierney et al. (1987) *Planta* 172: 356–363; E8 promoter, Deikman et al. (1988) *Embo J.* 7 (11) 3315–3320; 2AII promoter, Pear et al. (1989) *Plant Mol. Biol.* 13: 639–651; acid chitinase promoter, Samac et al. (1990) *Plant Physiol.* 93: 907–914;

The promoter selected should be capable of causing sufficient expression of the desired protein alone, but especially when used with the HSP70 intron, to result in the production of an effective amount of the desired protein to cause the plant cells and plants regenerated therefrom to exhibit the properties which are phenotypically caused by the expressed protein. In particular, the enhanced CaMV35S promoter or the FMV35S promoter is useful in the present invention. The enhanced CaMV35S promoter causes sufficient levels of the protein mRNA sequence to be produced in plant cells.

The mRNA produced by the promoter contains a 5' non-translated leader sequence. This non-translated leader sequence can be derived from any suitable source and can be specifically modified to increase translation of the mRNA. The 5' non-translated region can be obtained from the promoter selected to express the gene, the native 5' leader sequence of the gene or coding region to be expressed, vital RNAs, suitable eucaryotic genes, or a synthetic gene sequence. The present invention is not limited to the construct presented in the following examples, wherein the non-translated region is derived from 45 nucleotides from the eCaMV35S promoter. The non-translated leader sequence can also be derived from an unrelated promoter or viral coding region as described.

The 3' non-translated region of the chimeric plant gene contains a polyadenylation signal that functions in plants to cause the addition of polyadenylated ribonucleotides to the 3' end of the mRNA. Examples of suitable 3' regions are the 3' transcribed, non-translated regions containing the polyadenylation signal of Agrobacterium tumor inducing (Ti) plasmid genes, such as the NOS gene, and plant genes such as the soybean storage protein genes and the small subunit promoter of the RUBISCO gene. An example of a preferred 3' region is that from the nopaline synthase gene as described in the examples below.

In order to determine that the isolated HSP70 intron sequence included the desired intron region and to demonstrate the effectiveness and utility of the isolated HSP70 intron, reporter genes were inserted into plant cassette vectors. The reporter genes chosen were the *E. coli* β-glucuronidase (GUS) coding sequence and the luciferase (LUX) coding sequence.

The chimeric gene of this invention may contain any structural gene encoding a protein to be expressed in plants. An example of a suitable protein for use in this invention is EPSP synthase (5-enolpyruvyl-3-phosphoshikimate synthase; EC:25.1.19) which is an enzyme involved in the shikimic acid pathway of plants. The shikimic acid pathway provides a precursor the the synthesis of aromatic amino acids essential to the plant. Specifically, EPSP synthase catalyzes the conversion of phosphoenol pyruvate and 3-phosphoshikimic acid to 5-enolpyruvyl-3-phosphoshikimate acid. A herbicide containing N-phosphonomethylglycine inhibits the EPSP synthase enzyme and thereby inhibits the shikimic acid pathway of the plant. The term "glyphosate" is usually used to refer to the N-phosphonomethylglycine herbicide in its acidic or anionic forms. Novel EPSP synthase enzymes have been discovered that exhibit an increased tolerance to glyphosate containing herbicides. In particular, an EPSP synthase enzyme having a single glycine to alanine substitution in the highly conserved region having the sequence: -L-G-N-A-G-T-A- located between positions 80 and 120 in the mature wild-type EPSP synthase amino add sequence has been shown to exhibit an increased tolerance to glyphosate and is described in the commonly assigned U.S. Pat. No. 4,971,908 entitled "Glyphosate-Tolerant 5-Enolpyruvyl-3-Phosphoshikimate Synthase," the teachings of which are hereby incorporated by reference hereto. Methods for transforming plants to exhibit glyphosate tolerance are discussed in the commonly assigned U.S. Pat. No. 4,940,835 entitled "Glyphosate-Resistant Plants," the disclosure of which is specifically incorporated herein by reference. A glyphosate-tolerant EPSP synthase plant gene encodes a polypeptide which contains a chloroplast transit peptide (CTP) which enables the EPSP synthase polypeptide (or an active portion thereto) to be transported into a chloroplast inside the plant cell. The EPSP synthase gene is transcribed into mRNA in the nucleus and the mRNA is translated into a precursor polypeptide (CTP/mature EPSP synthase) in the cytoplasm. The precursor polypeptide is transported into the chloroplast.

Another example of a suitable protein for use in this invention is glyphosate oxidoreductase (GOX) enzyme which is an enzyme which converts glyphosate to aminomethylphosphorate and glyoxylate. By expressing the GOX enzyme in plants results in plants tolerant to glyphosate herbicide. The amino acid sequence of the GOX enzyme and modified genes encoding the GOX enzyme adapted for enhanced expression in plants are described in the commonly assigned patent application entitled "Glyphosate Tolerant Plants" having U.S. Ser. No. 07/717,370 filed Jun. 24, 1991, the teachings of which are hereby incorporated herein by reference.

Other examples of suitable proteins for use in this invention are *Bacillus thuringiensis* (B.t.) crystal toxin proteins which when expressed in plants protect the plants from insect infestation because the insect, upon eating the plant containing the B.t. toxin protein either dies or stops feeding. B.t. toxin proteins toxic to either Lepidopteran or Coleopteran insects may be used. Examples of particularly suitable DNA sequences encoding B.t. toxin protein are described in the commonly assigned patent application entitled "Synthetic Plant Genes and Method for Preparation," EP patent application 385,962 published Sep. 5, 1990, the teachings of which are hereby incorporated herein by reference.

Another example of an enzyme suitable for use in this invention is aminocyclopropane-1-carboxylic acid (ACC) oxidase which when expressed in plants delays fruit ripening by reducing the ethylene level in plant tissues. Examples of suitable DNA sequences encoding ACC oxidase are described in commonly assigned patent application entitled "Control of Fruit Ripening and Senescence in Plants," having U.S. Ser. No. 07/632,440 filed Dec. 26, 1990, the teachings of which are hereby incorporated herein by reference.

Other examples of enzymes suitable for use in this invention are acetolactate synthase, RNase to impart male sterility, Mariani et al. (1990) *Nature* 347: 737–741, and wheat germ agglutenin.

Another example of an enzyme suitable for use in this invention is ADP glucose pyrophosphorylase which when expressed in plants enhances the starch content. Examples of such starch enhancing enzymes are described in commonly assigned patent application entitled "Increased Starch Content in Plants," having U.S. Ser. No. 07/709,663 filed Jun. 7, 1991, the teachings of which are hereby incorporated herein by reference.

All oligonucleotides are synthesized by the method of Adams et al. (1983) *J. Amer. Chem. Soc.* 105, 661. The nucleotide bases adenine, thymine, uracil, cytosine and guanine are represented by the letters A, T, U, C and G, respectively.

This invention is suitable for any member of the monocotyledonous (monocot) plant family including, but not limited to, maize, rice, barley, oats, wheat, sorghum, rye, sugarcane, pineapple, yams, onion, banana, coconut, dates and hops. The present invention has particular applicability to the production of transgenic maize plants.

Any method suitable for transforming plant cells and regenerating transgenic plants may be used in the practice of this invention. Illustrative examples of methods suitable for regenerating transgenic plants are: corn (Fromm et al., 1990, *Bio/Technology* 8:833–839; and Gordon-Kamm et al., 1990, *The Plant Cell* 2:603–618); rice (Wang et al., 1988, *Plant Mol. Biol.* 11:433–439) and wheat (Vasil et al., 1991, *Bioftechnology* 8:743–747).

The production of fertile transgenic monocotyledonous plants involves several steps that together form the process. Generally, these steps comprise 1) culturing the desired monocot tissue to be transformed to obtain suitable starting material; 2) developing suitable DNA vectors and genes to be transferred into the monocot tissue; 3) inserting the desired DNA into the target tissue by a suitable method; 4) plant cells; 5) regenerating transgenic cells into fertile transgenic plants and producing progeny; and 6) analyzing the transgenic plants and their progeny for the presence of the inserted heterologous DNA or foreign gene.

A preferred method of the present invention utilizes embryogenic callus which is suitable for transformation and regeneration as the starting plant material. Embryogenic callus is defined as callus which is capable of being transformed and subsequently being regenerated into mature, fertile transgenic plants. The embryogenic callus preferably has a friable Type II callus phenotype that performs well in tissue culture. Embryogenic callus may be obtained using standard procedures known to those in the art (Armstrong, 1991, *Maize Genetic Newsletter* 65:92–93). Suitable maize embryogenic callus material may be obtained by isolating immature embryos from the maize plant 10 to 12 days after pollination. The immature embryos are then placed on solid culturing media to initiate callus growth. The immature embryos begin to proliferate as Type II callus after about one week and are thereafter suitable for use in the method of the present invention. Embryogenic callus suitable for use in the method of the present invention may be obtained from the initial callus formation on the immature embryos or may be from older established callus cultures up to 2 years in age. It is preferred, however, that younger callus cultures be used to enhance the recovery of fertile transgenic plants. Embryogenic callus that is between one week and six months of age is preferred and embryogenic callus between one week and four weeks of age is most preferred. The embryogenic callus of the present invention is considered "primary" callus in that it has never been processed through or maintained as a suspension culture. A suspension culture is defined as callus that has been broken up and placed in a liquid solution for a period of 1 to 9 months to establish a growing suspension culture. The embryogenic callus suitable for use in the present invention has never been through a suspension culture process or ever maintained as a suspension culture.

The preferred method of the present invention is applicable to any monocot embryogenic callus that is capable of regenerating into mature fertile transgenic plants and does not depend on a particular genotype, inbred, hybrid or species of the monocot desired to be transformed. It is to be understood, however, that the efficiency of the process will probably vary depending on the culturability and transformability of the particular plant line being used. In the present invention, a preferred maize embryogenic callus may be obtained from an A188×B73 $F_1$ genotype hybrid line, or a derivative of this line, or an "Hi-II" genotype. Any genotype that can give rise to a friable Type II callus material is suitable and will be useful in the method of the present invention. The embryogenic callus may be initiated and maintained in any suitable tissue culture media that will promote the growth of callus of the desired phenotype. Suitable tissue culture media are known to those skilled in the art of plant genetic engineering. The A188×B73 $F_1$ hybrid line and Hi-II line have been successfully initiated, maintained and regenerated in the tissue culture media described in Table 1.

TABLE 1

N6 1-100-25 (1 L)
4.0 grams/L Chu ($N_6$) Basal Salts (Sigma C-1416)
1.0 ml/L Eriksson's Vitamin Mix (1000× stock made from Sigma E-1511 Powder)
1.25 ml/L 0.4 mg/ml thiamine HCl
20 g/L Sucrose
1 ml/L 2, 4 D (1 MG/ML) (2, 4 D=2, 4, dichlorophenoxyacetic acid)
2.88 g/L L-proline
0.1 g/L Vitamin Free Casamino Acids
 (from Difco; Bacto Vitamin Assay Casamino Acids, Catalog#0288-01-2).
Adjust pH to 5.8, and add 2 g/L Gelrite or Phytagel, autoclave for 30 minutes, and pour into 25×100 mm petri dishes in sterile hood.
N6 1-0-25
same as N6 1-100-25 except that no Casamino Acids are used.
N6 2-100-25
same as N6 1-100-25 above, except that 2 ml/L 2,4 D (1mg/ml) is used.
N6 2-0-0
same as N6 1-100-25 above, except 2 ml/L 2,4D (1 mg/ml) and no Vitamin Free Casamino Acids and no L-proline.
N6 6% 0 D
same as N6 2-0-0 above, except 60 g/L sucrose 0 ml/L 2,4 D, and 0 L-proline is used.
MS 0.1 D
4.3 g/L MS salts (Sigma), 20 g/L sucrose, 100 mg/L myo-inositol, 1.3 mg/L nicotinic acid, 0.25 mg/L each of thiamine-HCL, pyridoxine and calcium pantothenate, 0.1 ml/L of 2, 4 D (1 mg/ml), 10-7M Abscisic Acid (ABA).
MS0 D
same as MS 0.1 D above, except no 2, 4 D and no ABA.

Once the desired embryogenic callus culture has been obtained, transformation of the tissue is possible. A foreign gene or genes of interest may be transferred to the embryogenic callus. Generally, the DNA inserted into the embryogenic callus is referred to as heterologous DNA. The heterologous DNA may contain one or more foreign genes which may or may not be normally present in the particular monocotyledonous plant being transformed. A foreign gene is typically a chimeric or recombinant gene construct comprising a sequence of DNA which may or may not be normally present in the genome of the particular monocot being transformed. The heterologous DNA generally contains a foreign gene which comprises the necessary elements for expression of a desired polypeptide in the particular plant. Heterologous DNA suitable for transformation into a monocotyledonous plant typically contains foreign genes coding for a polypeptide which confers a desired trait or characteristic to the plant being transformed and screenable and selectable markers for determining whether the plant material has been transformed. A typical foreign gene capable of being expressed in a monocot contains a promoter which is capable of functioning in the monocot plant, an intron, a structural DNA coding sequence encoding a desired polypeptide and a polyadenylation site region recognized in monocotyledonous plants. A transgene is a gene or DNA sequence that has been transferred into a plant or plant cell. The details of construction of heterologous DNA vectors and/or foreign genes suitable for expression in monocots is known to those skilled in the art of plant genetic engineering. The heterologous DNA to be transferred to the monocot embryogenic callus may be contained on a single plasmid vector or may be on different plasmids.

The heterologous DNA to be used in transforming the embryogenic callus in the method of the present invention preferably includes a selectable marker gene which allows transformed cells to grow in the presence of a metabolic inhibitor that slows the growth of non-transformed cells. This growth advantage of the transgenic cells allows them to be distinguished, over time, from the slower growing or non-growing cells. Alternatively, or in conjunction with a selectable marker, a visual screenable marker such as the *E. coli* β-glucuronidase gene or firefly luciferase gene (deWet et al., 1987, *Mol. Cell Biol.* 7:725–737) also facilitates the recovery of transgenic cells.

Preferred selectable marker genes for use in the method of the present invention include a mutant acetolactate synthase gene or cDNA which confers tolerance to sulfonylurea herbicides such as chlorsulfuron, the NPTII gene for resistance to the antibiotic kanamycin or G418 or a bar gene for resistance to phosphinothricin or bialaphos.

The foreign gene selected for insertion into the monocot embryogenic callus can be any foreign gene which would be useful if expressed in a monocot. Particularly useful foreign genes to be expressed in monocots include genes which confer tolerance to herbicides, tolerance to insects, tolerance to viruses, and genes which provide improved or new characteristics which effect the nutritional value or processing capabilities or qualities of the plant. Examples of suitable agronomically useful genes include the insecticidal gene from *Bacillus thuringiensis* for conferring insect resistance and the 5'-enolpyruvyl-3'-phosphoshikimate synthase (EPSPS) gene and any variant thereof for conferring tolerance to glyphosate herbicides. As is readily understood by those skilled in the art, many other agronomically important genes conferring desirable traits can be introduced into the embryogenic callus in conjunction with the method of the present invention. One practical benefit of the technology of the present invention is the production of transgenic monocotyledonous plants that have improved agronomic traits.

Once the transformation vectors containing the desired heterologous DNA have been prepared, the DNA may be transferred to the monocot embryogenic callus through use of the microprojectile bombardment process which is also referred to as particle gun technology or the Biolistics process. The heterologous DNA to be transferred is initially coated onto a suitable microprojectile by any of several methods known to those skilled in the plant genetic engineering art. The microprojectiles are accelerated into the target embryogenic callus by a microprojectile gun device. The design of the accelerating device or gun is not critical so long as it can perform the acceleration function. The accelerated microprojectiles impact upon the prepared embryogenic callus to perform the gene transfer. When the microprojectile bombardment process is utilized, the DNA vector used to transfer the desired genes to the embryogenic callus is typically prepared as a plasmid vector and is coated onto tungsten or gold microprojectiles.

While any particle gun device may be used, the Biolistics PDS 1000 microprojectile gun device was used in the present invention. This device had a stopping plate configuration similar to commercially available stopping plates except that the lexan disk is ⅜" thick with a ³⁄₃₂"0 diameter hole through the disk center. The hole is enlarged at the upper surface to ⁷⁄₁₆" and this tapers in a countersunk arrangement to a depth of ¼" at which point it narrows to the ³⁄₃₂" diameter hole which does not have a taper for the remaining ¹⁄₁₈" thickness. The embryogenic target tissue is set at level 4 of this device which is one level from the bottom. The callus tissue sample was subjected to 1–3 shots. A shielding metal screen with 100µ openings is typically used on the shelf position immediately below the stopping plate. The process is performed under a suitable vacuum.

After the embryogenic calli have been bombarded with the desired heterologous DNA vector, the bombarded cells are grown for several days in non-selective culturing media and then placed on a selective media which inhibits the growth of the non-transformed cells, but allows transgenic cells to continue to grow. In about 8 weeks, the continued growth of the transgenic callus cells is apparent as a large growing calli and can be recovered and individually propagated. The transgenic embryogenic callus may then be regenerated into whole, mature transgenic plants pursuant to protocols for regenerating non-transformed embryogenic callus. Generally, when regenerated plants reach the three-leaf stage and have a well developed root system, they can be transferred to soil and hardened off in a growth chamber for two weeks before transfer to a greenhouse. The transformed embryogenic callus of the present invention respond well to regeneration procedures which work for non-transgenic callus.

Regenerated plants may subsequently be moved to a greenhouse and treated as normal plants for pollination and seed set. The confirmation of the transgenic nature of the callus and regenerated plants may be performed by PCR analysis, antibiotic or herbicide resistance, enzymatic analysis and/or Southern blots to verify transformation. Progeny of the regenerated plants may be obtained and analyzed to verify the hereditability of the transgenes. This illustrates the stable transformation and inheritance of the transgenes in the $R_1$ plant.

The following examples are provided to illustrate the method of the present invention and should not be interpreted in any way to limit the scope of the invention. Those skilled in the art will recognize that various modifications can be made to the methods described herein while not departing from the spirit and scope of the present invention.

DESCRIPTION OF PREFERRED EMBODIMENTS

EXAMPLE 1

Synthesis of HSP70 Intron by Polymerase Chain Reaction

The HSP70 intron was synthesized using the polymerase chain reaction from a genomic clone containing a maize HSP70 gene (pMON9502: Rochester et al., 1986, *Embo J.*, 5:451–458).

Two different oligonucleotide primers were used in the PCR reaction. The first primer consists of nucleotides 1–26 of SEQ ID NO:1 and contains a BglII site for cloning, ten nucleotides of flanking HSP70 exon 1 sequence, and ten bases of the intron sequence. The second primer is the reverse complement of bases 791 through 816 of SEQ ID NO:1 and contains 10 bp of intron sequence, 11 nucleotides of flanking 3' HSP70 exon sequence, and an NcoI site for cloning.

The "HSP70 intron," bases 7–812, contains the entire intron from a maize HSP70 gene (bases 17–799) plus 10 nucleotides from HSP70 exon 1 (bases 7–16) and 11 bases from HSP70 exon 2 (bases 800–812). Bases 1–6 and 813–816 include restriction sites used in cloning. Base 802 was a G in the native HSP70 exon, but has been replaced by an A for maximum enhancement of gene expression.

PCR was carried out in 100 ul reactions which contained 10 ng pMON9502 DNA, 40 pmole each of SEQ7 and SEQ20, 10 mM Tris-HCL (pH8.3), 50 mM KCl, 1.5 mM MgCl2, 0.01% (w/v) gelatin, 20 nmole of each dNTP, and 2.5 units Amplitaq DNA Polymerase (Perkin Elmer Cetus). Twenty eight cycles were run (denaturation 1 minute at 94° C., annealed 2 minutes at 50° C., and elongated 3 minutes at 72° C. per cycle).

The PCR reaction products were were purified by phenol:chloroform (1:1) extraction, followed by digestion with BglII and NcoI. The 0.8 kb HSP70 intron fragment was isolated by gel electrophoresis followed by purification over an Elutip-D column (Schlesser & Schuell). The HSP70 intron sequences were verified by the Sanger dideoxy DNA sequencing method. The sequence of the HSP70 intron is designated SEQ ID NO:1 and is shown in FIG. 1. The 0.8 kb HSP70 intron fragment was then cloned into the BglII and NcoI sites within the 5' untranslated leader region of pMON8677 to form pMON19433 as described below.

EXAMPLE 2

Effect of HSP70 Intron on Corn Gene Expression in Transient Assays

Figure 4:
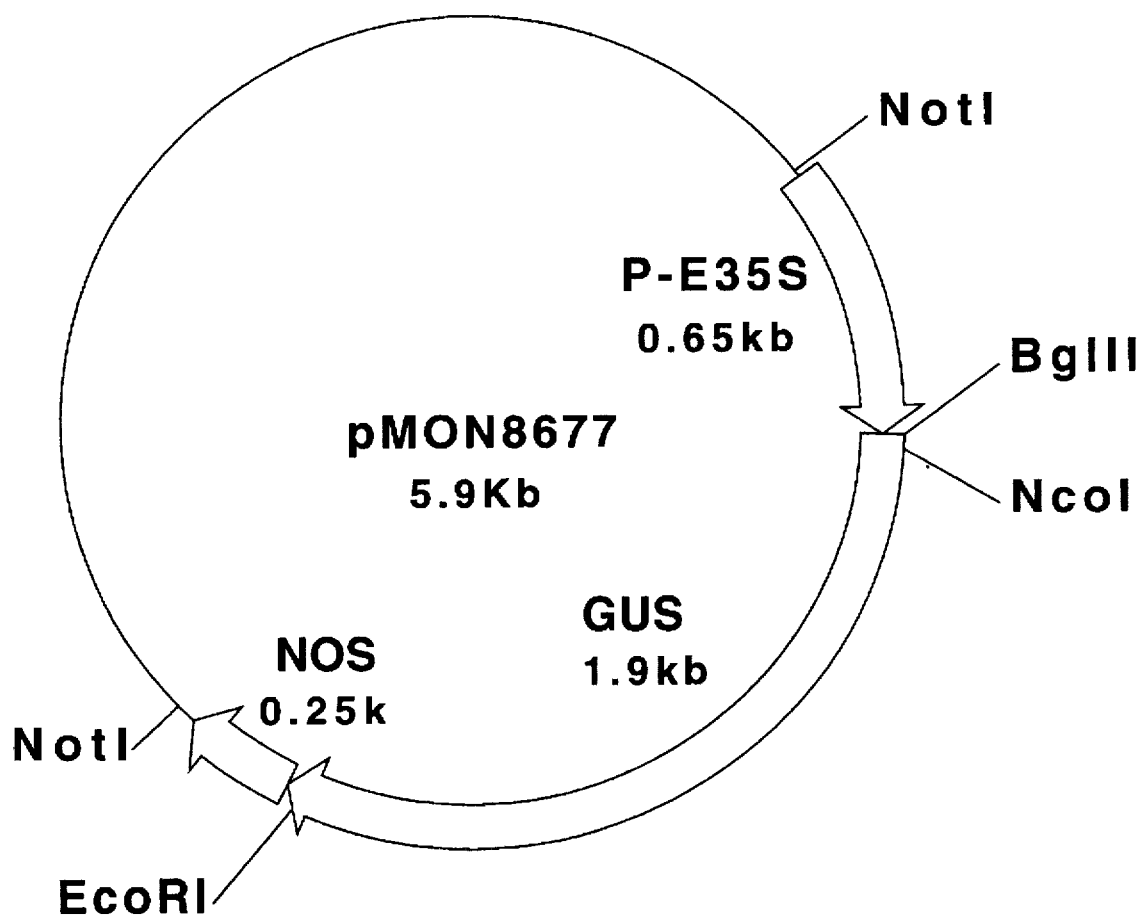
FIG. 4 illustrates a physical map of the plasmid pMON8677.
Figure 5:
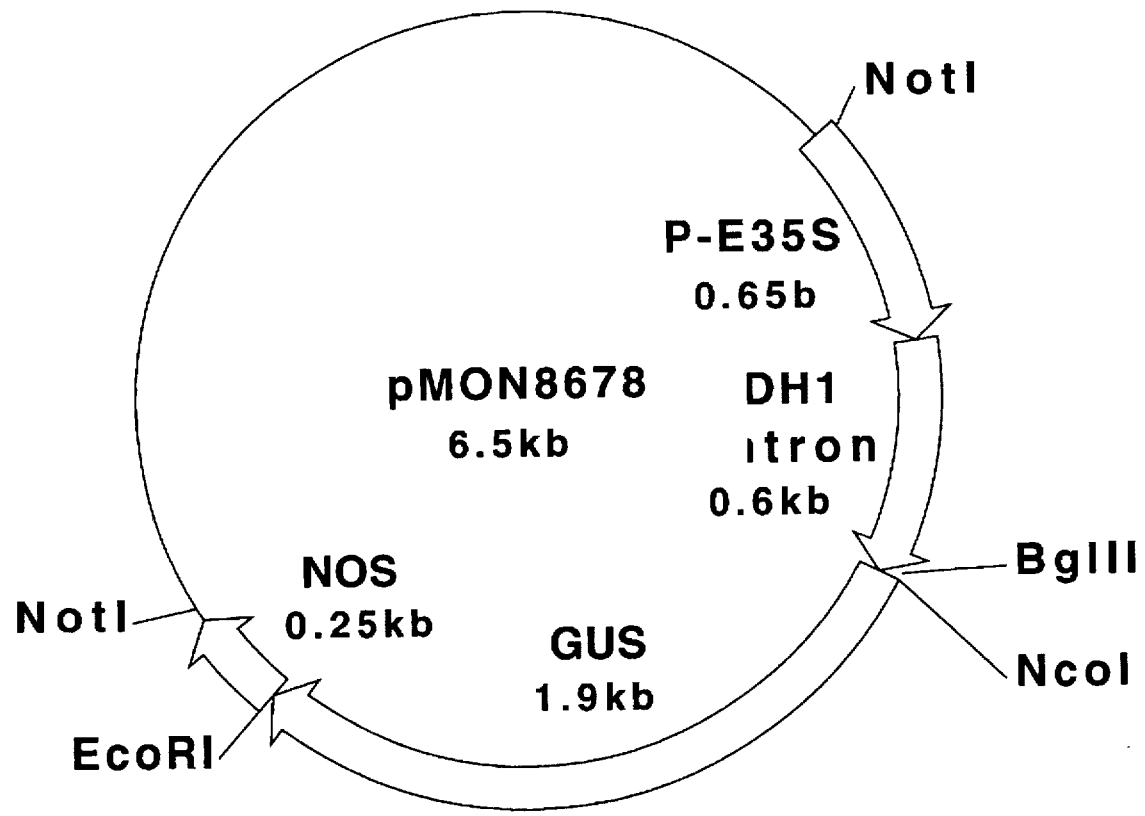
FIG. 5 illustrates a physical map of the plasmid pMON8678.
Figure 6:
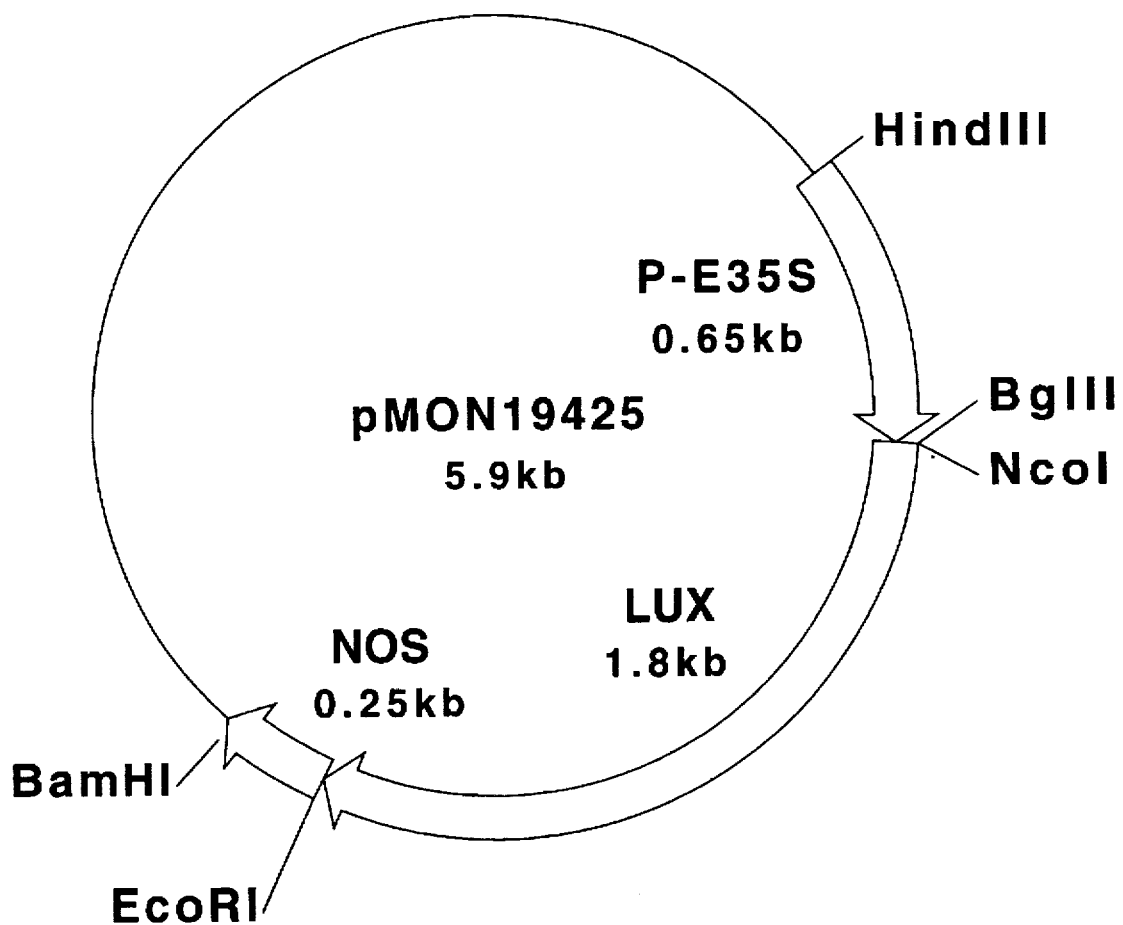
FIG. 6 illustrates a physical map of the plasmid pMON19425.
Figure 10:
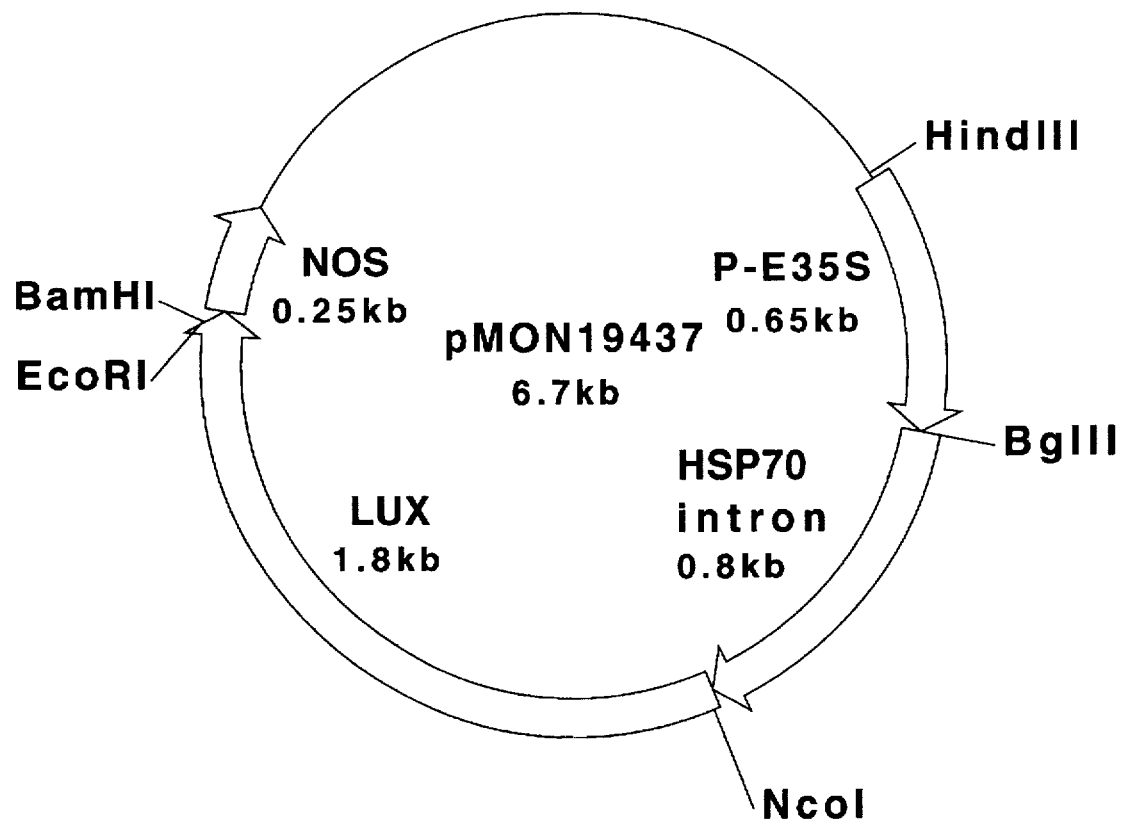
FIG. 10 illustrates a physical map of the plasmid pMON19437 comprising an HSP70 intron and a LUX coding sequence.
Figure 18:
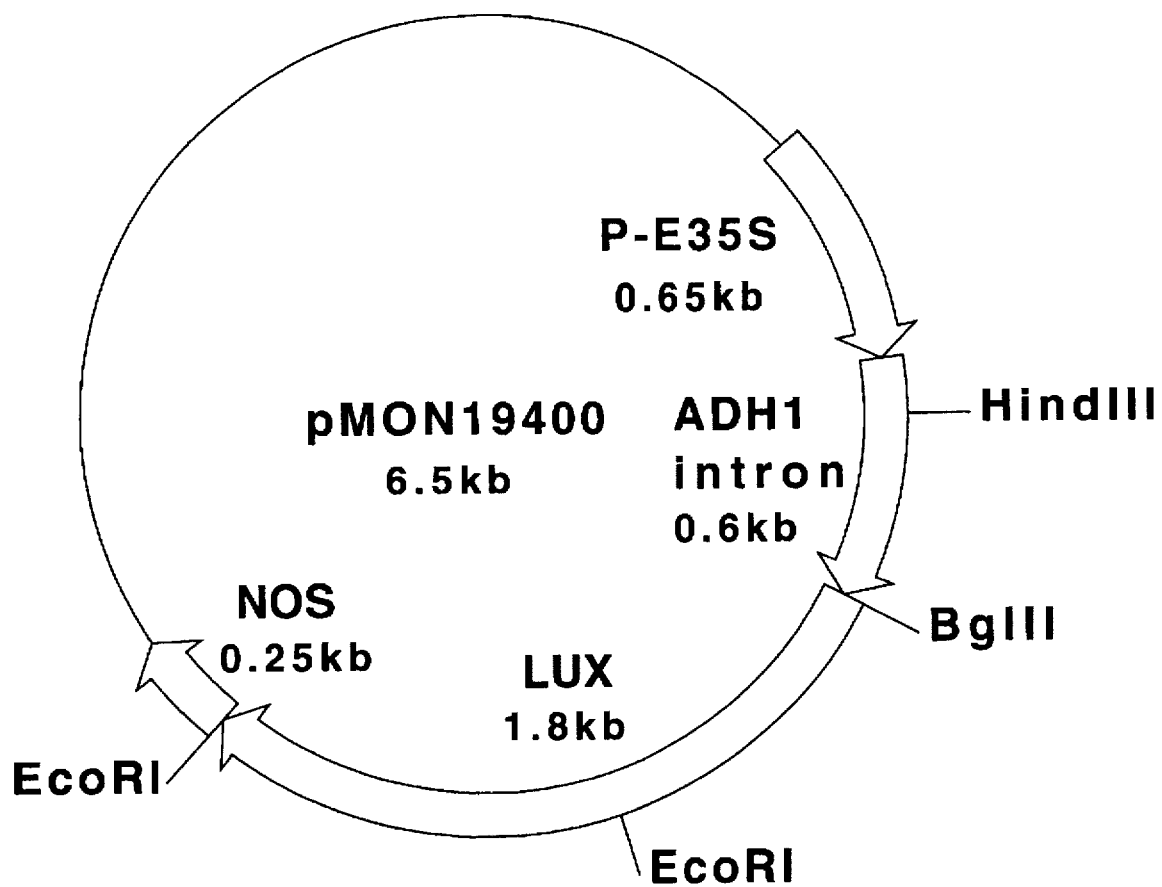
FIG. 18 illustrates a physical map of the plasmid pMON19643 comprising the HSP70 intron and the LUX coding sequence.

A. Preparation of pMON8677, pMON8678, pMON19433, pMON19425, pMON19400, and pMON19437.

pMON8677 (FIG. 4) was constructed using well characterized genetic elements. The 0.65 kb cauliflower mosaic virus (CaMV) 35S RNA promoter (e35S) containing a duplication of the −90 to −300 region (Kay et al., 1987, *Science* 236:1299–1302), the 1.9 kb coding sequences from the *E. coli* β-glucuronidase (GUS) gene (Jefferson et al., 1986, *PNAS* 83:8447–8451) and a 0.25 kb fragment containing the 3' polyadenylation sequences from the nopaline synthase (NOS) gene (Fraley et al., 1983, *Proc. Natl. Acad. Sci.* 80:4803–4807) were each inserted into pUC119 (Yanisch-Perron et al., 1985, *Gene* 33:103–119) to form the plant gene expression vector pMON8677.

pMON8678 (FIG. 5) was formed by inserting a 0.6 kb fragment containing the first intron from the ADH1 gene of maize (Callis et al., 1987, *Genes and Dev.* 1:1183–1200) into pMON8677 as described in Vasil et al. (1991) *Bio/Technology* 9:743–747. The monocot expression region in pMON8678 is identical to pMON8677 except that it contains the ADH1 intron fragment in the 5' untranslated leader.

pMON19433 (FIG. 9) was constructed by cloning the BglII-NcoI digested PCR fragment containing the maize HSP70 intron sequences into the NcoI-BglII sites in pMON8677 to produce a monocot expression vector equivalent to pMON8677 except that it contains the maize HSP70 intron fragment in the 5' untranslated leader.

pMON19425 (FIG. 6) was constructed by inserting the 0.65 kb cauliflower mosaic virus (CaMV) 35S RNA promoter (e35S) containing a duplication of the −90 to −300 region, the 1.8 kb fragment of the firefly luciferase (LUX) gene (Ow et al., 1986, *Science* 234:856–859; DeWet et al., 1987, *Mol. Cell Biol.* 7:725–737), and the 0.25 kb fragment containing the NOS polyadenylation sequences into pUC119 (Yanisch-Perron et al., 1985, supra).

pMON19400 (FIG. 18) was formed by replacing the GUS coding sequence in pMON8678 with the 1.8 kb fragment of the LUX gene. The monocot expression region in pMON19400 is identical to pMON19425 except that it contains the ADH1 intron fragment in the 5' untranslated leader.

pMON19437 (FIG. 10) was constructed by cloning HSP70 intron sequence from pMON19433 as a 0.8 bp NcoI-BglII fragment into the NcoI-BglII sites in pMON19425 to produce a monocot expression vector equivalent to pMON19425 except that it contains the maize HSP70 intron fragment in the 5' untranslated leader.

B. Analysis of gene expression using transient assays.

Two transient gene expression systems were used to evaluate expression from the HSP70 intron and ADH1 intron vectors in corn cells. Two corn cell lines were transformed shooting corn cells or tissues by high velocity projectiles coated with the indicated plasmid DNA. One cell line was Black Mexican Sweet (BMS) corn, a nonregenerable corn callus suspension cells. The other cell line was BC17 corn used as tissue from corn leaves obtained from 4 week old plants from the innermost leaves at the nodes around the tassel primordia.

Plasmid DNAs were prepared by using standard alkaline lysis followed by CsCl gradient purification (Maniatis et al., 1982, *Molecular Cloning: A Laboratory Manual*, CSH Labs). Plasmid DNA was precipitated onto tungsten M10 particles by adding 25 ul of particles (25 mg/ml in 50% glycerol), 3 ul experimental plasmid DNA (1 ug/ul), 2 uL internal control plasmid DNA (1 ug/ul), 25 uL 1M calcium chloride, and 10 uL 0.1M spermidine, and vortexing briefly. The particles were allowed to settle for 20 minutes, after which 25 ul of supernatant was removed and discarded. Two independent particle preparations were done for each vector evaluated.

The particle preparations were then bombarded into the tissue/cells as follows. Each sample of DNA-tungsten was sonicated briefly and 2.5 ul was bombarded into the tissue/cells contained on one plate using a PDS-1000 (DuPont) Biolistics particle gun. Three plates of tissue/cells were bombarded from each particle preparation.

The tissue/cells were harvested after a 24–48 hours incubation (25° C., dark). The cells/tissues from the three bombarded plates from each particle preparation were combined, frozen with liquid nitrogen, and ground to a fine white powder with a mortar and pestle. Each sample was thawed on ice in 1 ml of GUS extraction buffer (GEB: 0.1M KPO4 pH7.8, 1 mM EDTA, 10 mM DTT, 0.8 mM PMSF, and 5% glycerol). The samples were then vortexed and centrifuged at 8 K. for 15 minutes at 5° C., and the supernatant was transferred to a fresh tube. When enzyme assays were not performed immediately, the samples were frozen on dry ice and stored at −80° C.

Transient β-glucuronidase gene expression was quantitated using a fluorometric assay (Jefferson et al., 1987, *Embo. J.* 6:3901–3907). Fifty ul crude extract was assayed in one ml GEB containing 2 mM 4-methyl umbelliferyl glucuronide. At 0, 10, 20, and 30 minute timepoints, 100 ul aliquots were removed and the reaction terminated by addition to 2 ml 0.2M Na2CO3. Fluorescence from each sample was then determined using a Hoescht DNA Fluorometer (model TKO 100). GUS activity is expressed as the slope of fluorescence versus reaction time.

Quantitative luciferase assays were performed as follows. 50 ul of extract was added to a cuvette containing 0.2 mls of 25 mM Tricine pH7.8, 15 mm MgCl2, 5 mM ATP, and 0.5 mg/ml BSA. The 0.5 mM luciferin substrate was automatically dispensed by the luminometer (Berthold Bioluminat LB9500C) and the peak luminescence measured during a 10 second count at 25° C. Three to ten reactions were run per sample. LUX activity is expressed as the mean light units per ul of extract.

All vectors tested were co-bombarded with internal control vectors which encoded proteins whose enzymatic activities were distinct from those of the vectors being evaluated. For example, in the experiments in which LUX vectors being evaluated, pMON8678 (GUS) was used as the internal control vector, and when GUS vectors being tested pMON19400 (LUX) was used as the internal control vector. To correct for any variability in the procedure the results were then expressed as a ratio of the experimental reporter gene expression to the internal control reporter gene expression. The results are summarized in Table 2.

As shown in Table 2A, the HSP70 intron vectors gave significantly increased gene expression in BMS suspension cells when compared to vectors containing no intron (40 fold increase) or the ADH1 intron (4 fold increase) vectors. This effect was observed using either GUS or or LUX as the reporter gene. Table 2B shows that this effect is not limited to the BMS cell system. In the leaf transient gene expression assays, the HSP70 intron vector showed an 8.7 times GUS expression level over the control containing no intron, whereas, the ADH1 intron showed only a 1.6 times GUS expression level over the control containing no intron.

TABLE 2

Effects of Introns on Gene Expression in Transient Assays

| Intron | Relative GUS (vector) | Relative LUX (vector) |
|---|---|---|
| A. Effect of introns on transient gene expression in BMS cells. | | |
| no intron | 1X (pMON8677) | 1X (pMON19425) |
| ADH1 | 4X (pMON8678) | 4X (pMON19400) |
| HSP70 | 40X (pMON19433) | 40X(pMON19437) |
| Effect of introns on transient gene expression in maize leaf tissue. | | |
| no intron | 1X (pMON8677) | |
| ADH1 | 1.6X (pMON8678) | |
| HSP70 | 8.7X (pMON19433) | |

EXAMPLE 3

Effect of HSP70 intron on gene expression in stably transformed nonregenerable corn cultures A. Production of stably transformed BMS cell lines.

Figure 19:
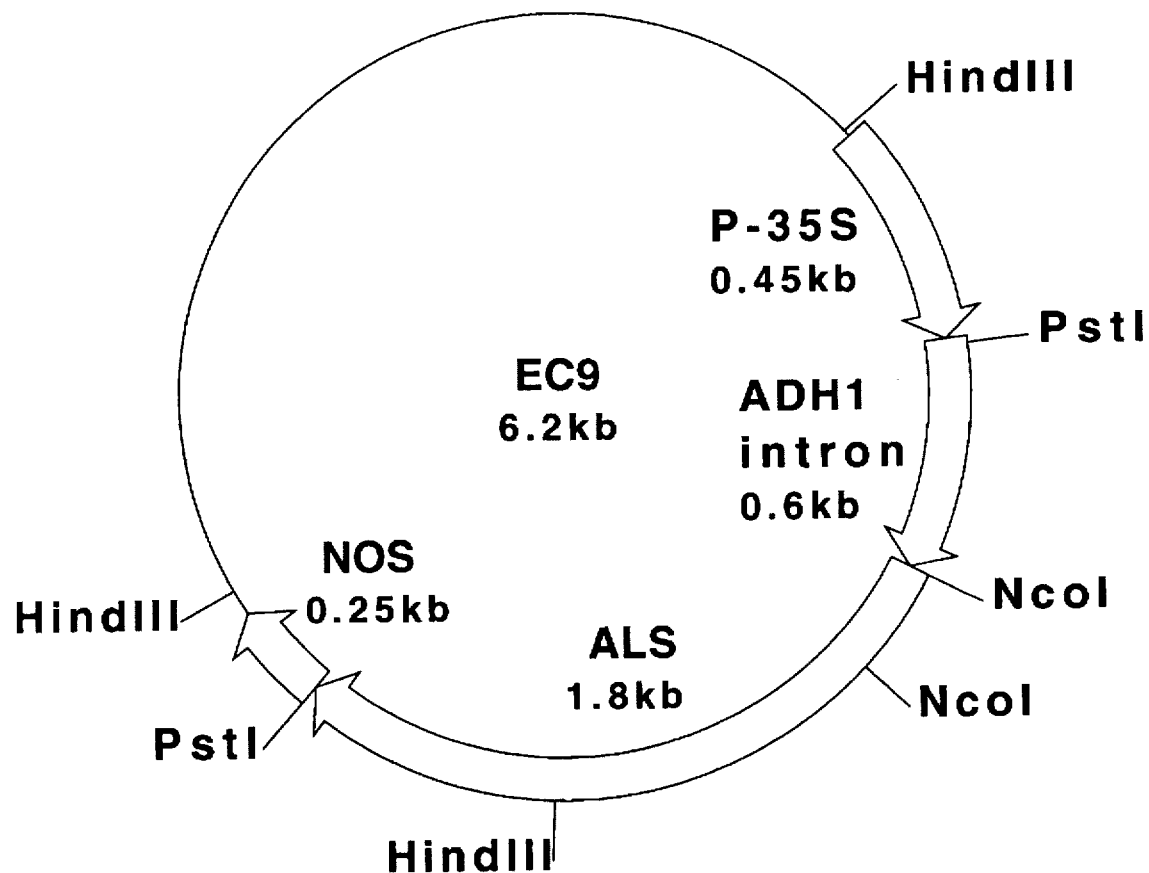
FIG. 19 illustrates a physical map of the plasmid EC9 comprising the ADH1 intron.

Black Mexican Sweet corn suspension cells were transformed by particle gun bombardment essentially as described above. Plasmid DNA for bombardment was prepared and precipitated onto tungsten M10 particles by adding 12.5 ul of particles (25 mg/ml in 50% glycerol), 2.5 ul plasmid DNA (1 ug/ul), 12.5 uL 1M calcium chloride, and 5 uL 0.1M spermidine, and vortexing briefly. The particles were allowed to settle for 20 minutes, after which 12.5 ul of supernatant was removed and discarded. Each sample of DNA-tungsten was sonicated briefly and 2.5 ul was bombarded into the embryogenic cultures using a PDS-1000 biolisitics particle gun (DuPont). EC9 (FIG. 19), a plasmid containing an acetolactate synthase gene, was included for use in chlorsulfuron selection for transformed control cells. A second plasmid containing the test construct was co-precipitated with EC9.BMS cells were plated on filters and bombarded using a PDS-1000 (DuPont) particle gun. After bombardment, the cells were transferred to MS liquid medium for 1 day and then plated onto solid medium containing 20 ppb chlorsulfuron. After approximately 4 weeks, chlorsulfuron resistant calli were selected and grown up for analysis of gene expression.

B. Effect of the HSP70 intron on GUS expression.

Plasmids containing the GUS gene and no intron (pMON8677), ADH1 intron (pMON8678), or HSP70 intron (pMON19433) were bombarded into BMS cells and stably transformed lines were produced as described above. Chlorsulfuron resistant lines were selected and then scored for GUS expression by histochemical staining (Jefferson et al., 1987, Embo. J. 6:3901–3907). As shown in Table 3A, the transformations with the HSP70 intron vector showed a significantly higher proportion of co-expression of the unselected GUS marker than did the transformation with either the vector containing the ADH1 intron or no intron. Since more chlorsulfuron resistant calli were above the threshold of detection histochemical GUS staining, it is likely that the HSP70 intron vectors express at higher levels than the ADH1 or no intron vectors. To confirm this, GUS activity was quantitated in extracts from ten independent GUS positive transformants from each vector (for pMON8677, the one GUS positive callus was assayed; nine others were chosen randomly). The data from these assays is shown in Table 3B. These results indicate that the HSP70 intron enhances GUS expression in stably transformed cell lines to an even greater extent than was observed in transient gene expression analyses. The mean level of GUS expression observed with the lines containing the HSP70 intron vector was approximately 80 fold over that observed in lines containing the ADH1 intron vector. The best of the ten HSP70 lines expresses over 100 fold more GUS than the best ADH1 line and approximately 800 fold over the best line without an intron.

TABLE 3

Effect of Introns on GUS Expression in Stable Transformants

A. GUS expressing BMS calli - number and percentage.

| Class | pMON8677 No Intron | pMON8678 ADH1 intron | pMON19433 HSP70 intron |
|---|---|---|---|
| — | 79(99%) | 48(67%) | 28(47%) |
| + | 0(0%) | 14(19%) | 2(3%) |
| ++ | 1(1%) | 9(13%) | 7(12%) |
| +++ | 0(0%) | 1(1%) | 22(37%) |
| | 80 | 72 | 59 |

B. Levels of GUS expression in BMS calli.

| Vector | Intron | Range** | Mean** |
|---|---|---|---|
| pMON8677 | none | 0–38 | N.D. |
| pMON8678 | ADH1 | 28–219 | 95 + 75 |
| pMON19433 | HSP70 | 1594–29,629 | 7319 ± 9016 |

*— no cells show expression
+ a few cells show GUS expression
++ some cells show GUS expression
+++ all cells show strong GUS expression
**(pmol/min/mg)

EXAMPLE 4

Figure 9:
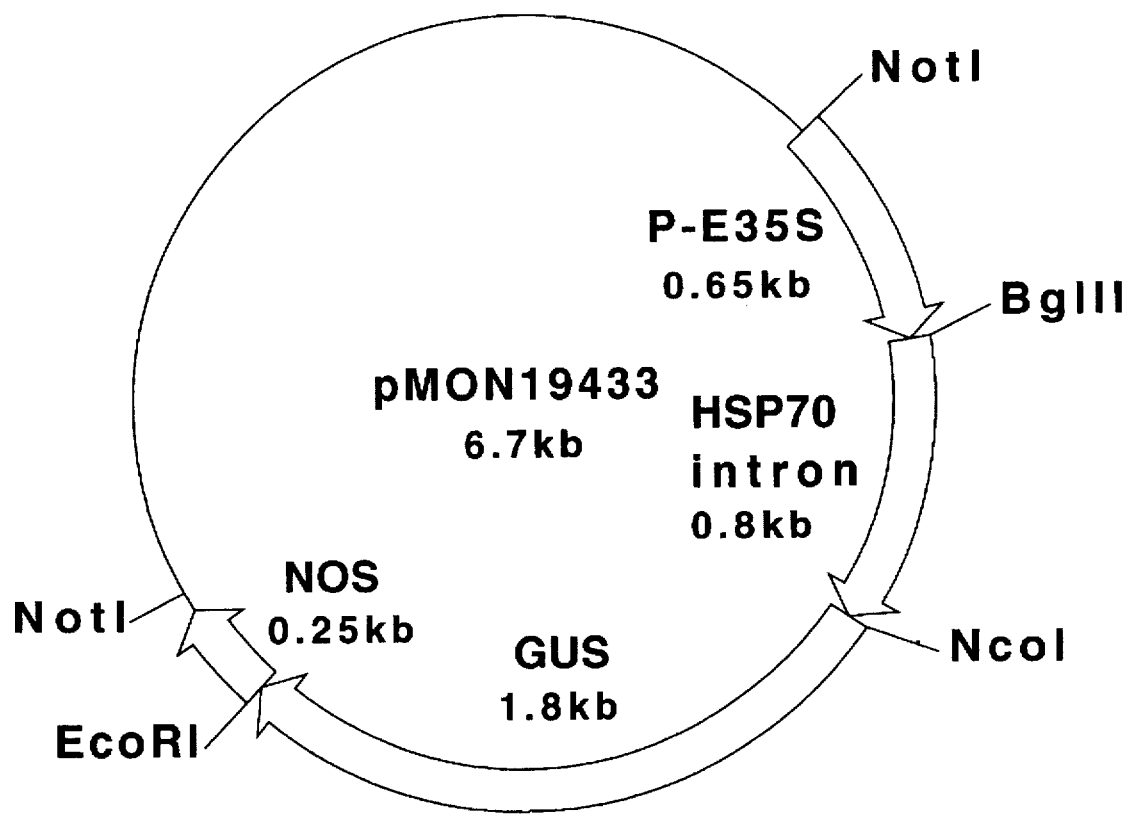
FIG. 9 illustrates a physical map of the plasmid pMON19433 comprising an HSP70 intron and a GUS coding sequence.
Figure 11:
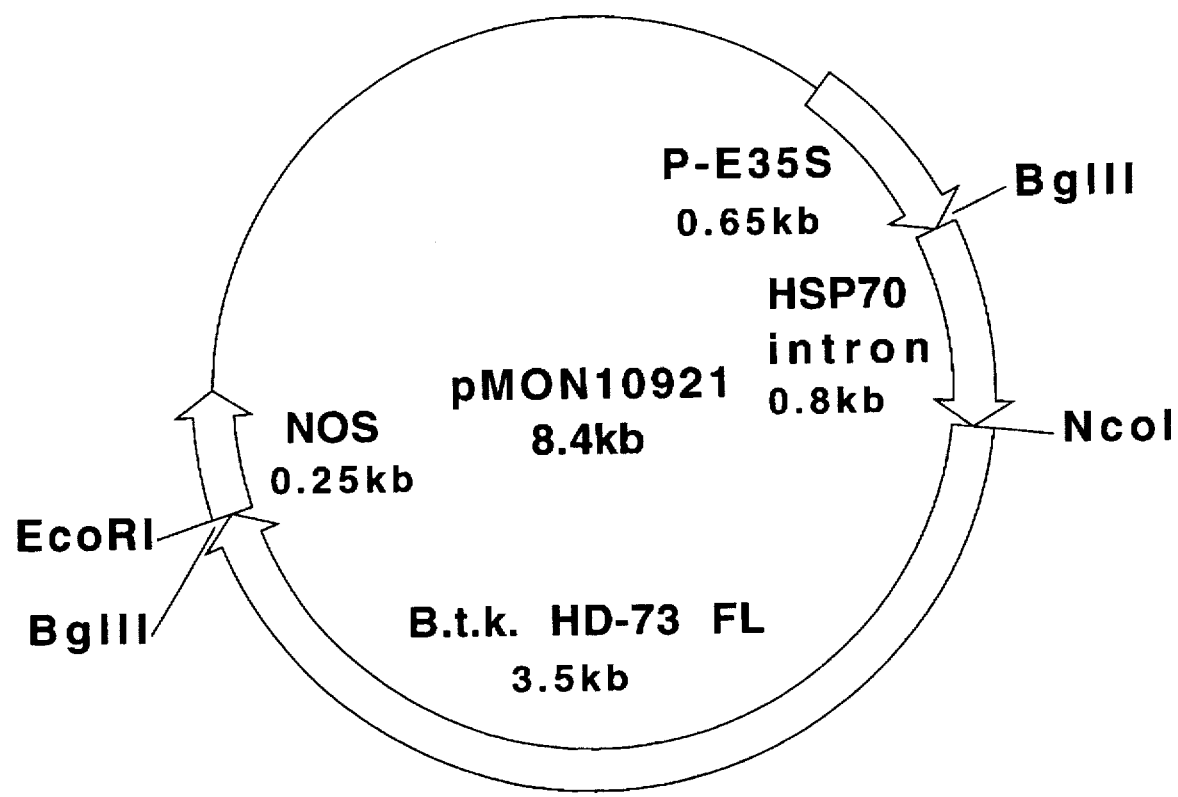
FIG. 11 illustrates a physical map of the plasmid pMON10921 comprising an HSP70 intron and a Bt.k.-HD73 coding sequence.
Figure 20:
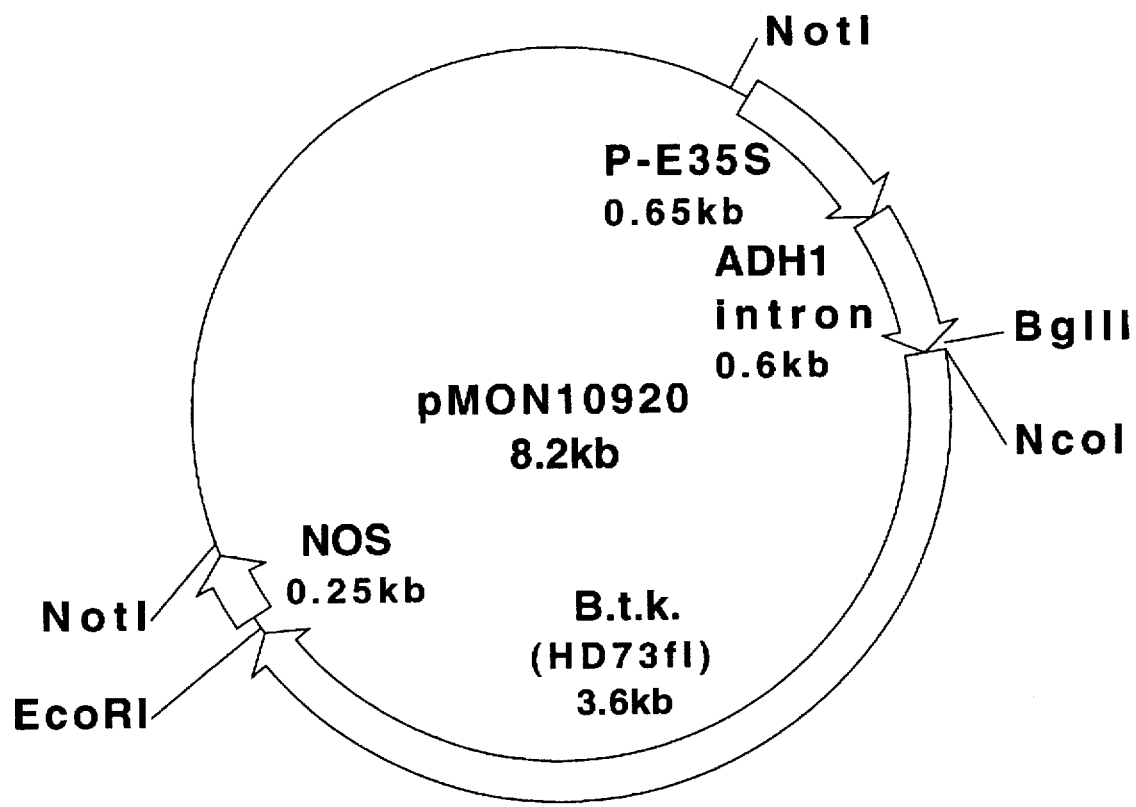
FIG. 20 illustrates a physical map of the plasmid pMON10920 comprising a B.t.k. coding sequence—HD73 full length.
Figure 21:
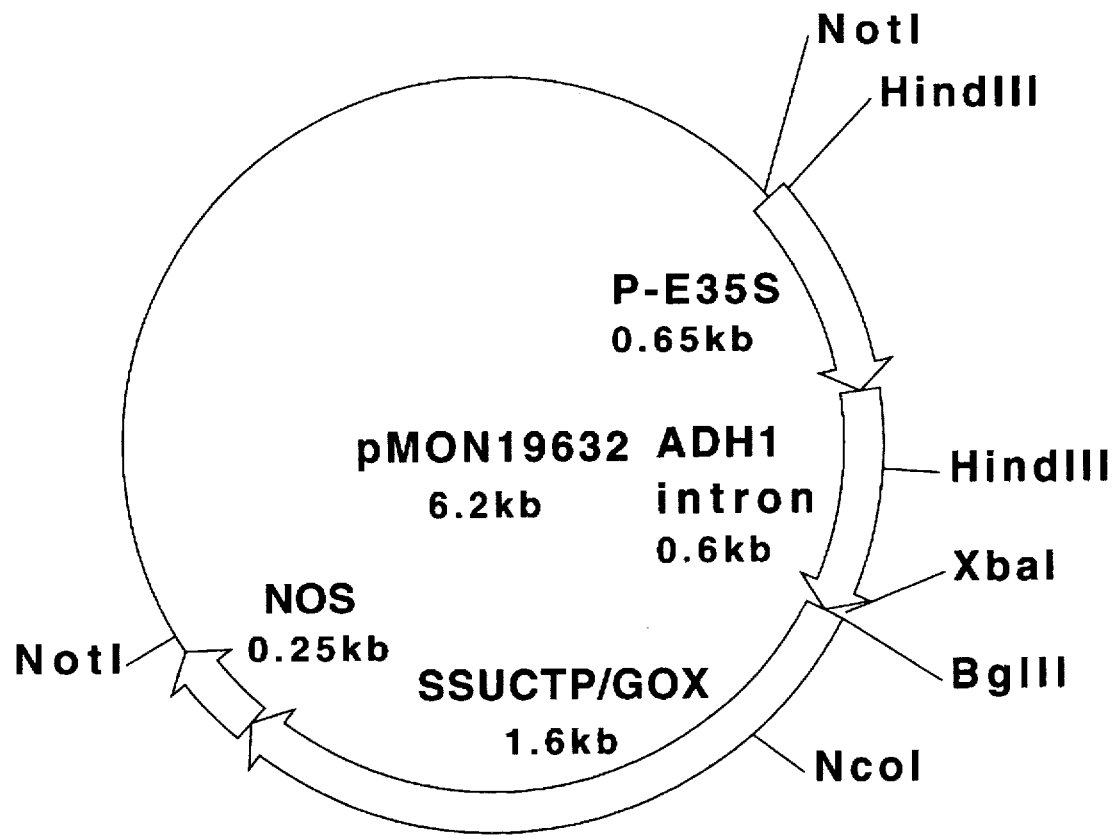
FIG. 21 illustrates a physical map of the plasmid pMON19632 comprising a ADH1 intron and a GOX coding sequence.

Effect of HSP70 Intron on B.t.k. Expression in Stably Transformed BMS Cell Lines We have similarly examined the effect of the HSP70 intron on expression of the commercially important B.t.k. gene. Two plasmids were constructed that only differed by the intron they contained: pMON10920 (e35S/ADH1/B.t.k./NOS) and pMON10921 (e35S/HSP70/B.t.k./NOS). Each contained a 3.6 kb fully synthetic gene encoding the Bacillus thuringiensis (B.t.k.) insect control protein described by Adang et al. (1985) *Gene* 36: 289–300. Expression of this gene in plants results in insect resistance. pMON10920 (FIG. 20) was constructed by inserting the 3.6 kb NcoI/EcoRI fragment containing the B.t.k. into pMON8678 (FIG. 5), replacing the 1.9 kb GUS fragment. pMON10921 (FIG. 11) was constructed similarly, except that the 3.6 kb NcoI/EcoRI fragment containing the B.t.k. coding sequence was inserted into pMON 19433 (FIG. 9).

BMS lines were co-transformed with each of these plasmids and EC9 (ALS) as described in Example 3A. Approximately thirty independent chlorsulfuron resistant lines were generated in each transformation. These calli were tested for Tobacco Hornworm (THW) toxicity, and the insect resistant lines were assayed further. The amount of B.t.k. protein in soluble extracts from each THW resistant callus was measured by ELISA and expressed as a percentage of total protein. Of the 11 insect positive lines containing the ADH1 intron vector (pMON10920), only one line contained enough B.t.k. protein to be detected in the ELISA assay. The amount was $0.4 \times 10^{-5}\%$. Twenty of the 29 THW resistant lines containing the HSP70 intron vector (pMON10921) produced enough protein for detection by ELISA. The average amount was $5.1 \times 10^{-5}\%$ with a range of $<0.01–10.5 \times 10^{-5}\%$. When the mean B.t.k. protein levels are compared, the HSP70 intron vector increases expression 12 fold over the ADH1 intron vector.

EXAMPLE 5

Figure 22:
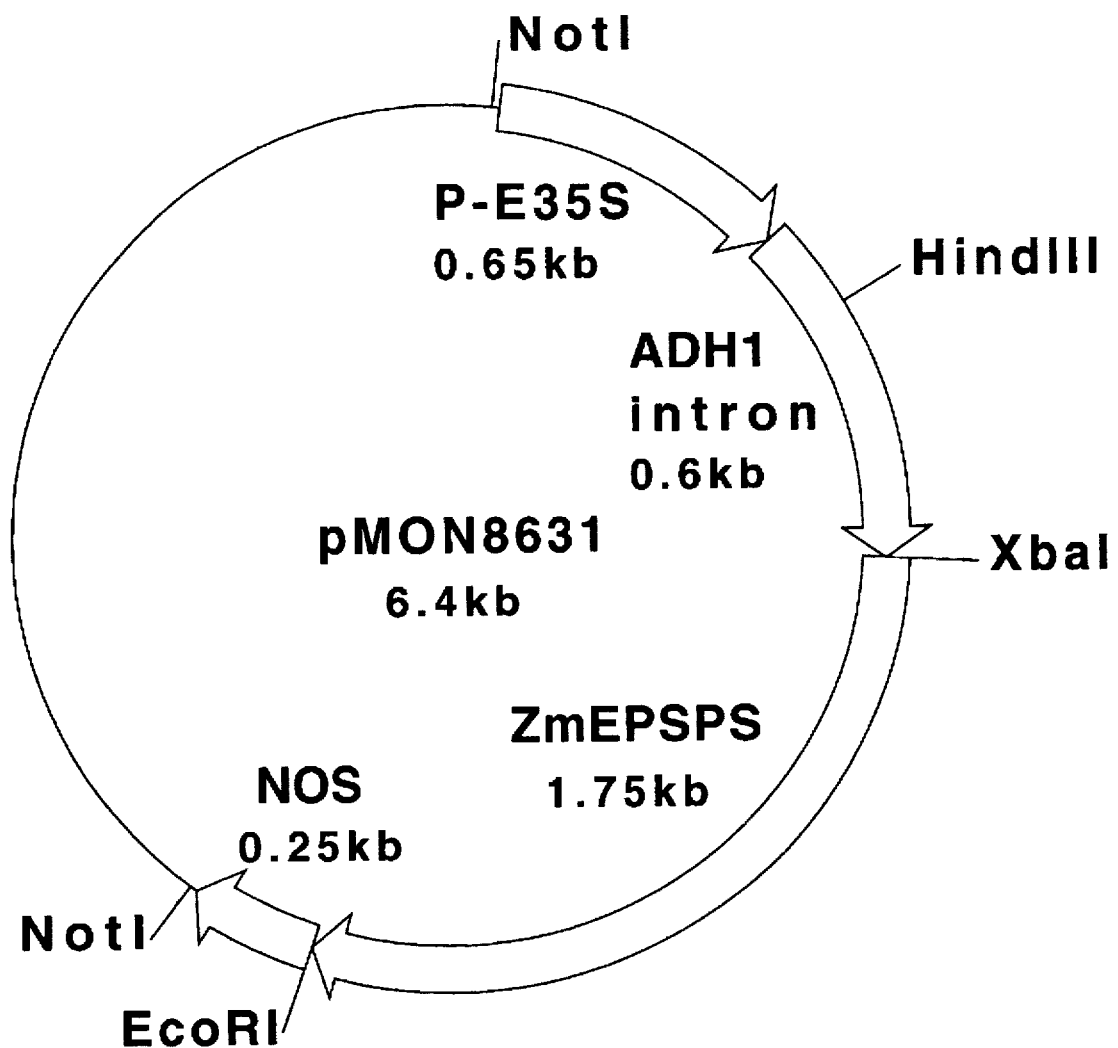
FIG. 22 illustrates a physical map of the plasmid pMON8631 comprising a maize EPSPS coding sequence.

Effect of HSP70 Intron on GOX Expression in BMS Transformants pMON19632 and pMON 19643 were constructed to examine the effects of introns on GOX expression. Both vectors contain a gene fusion composed of the N-terminal 0.26 Kb chloroplast transit peptide sequence derived from the *Arabidopsis thaliana* SSU 1a gene (SSU CTP) (Timko et al., 1988, *The Impact of Chemistry on Biotechnology*, ACS Books, 279–295) and the C-terminal 1.3 Kb synthetic GOX gene sequence. The GOX gene encodes the enzyme glyphosate oxidoreductase which catalyzes the conversion of glyphosate to herbicidally inactive products, aminomethylphosphonate and glyoxylate. Plant expression of the gene fusion produces a pre-protein which is rapidly imported into chloroplasts where the CTP is cleaved and degraded releasing the mature GOX protein (della-Cioppa et al., 1986, *Proc. Natl. Acad. Sci. U.S.A.* 83: 6873–6877).

pMON19632 (FIG. 22) was constructed in the same manner as pMON8678 by inserting the SSU•CTP-GOX fusion as a 1.6 kb BglII-EcoRI fragment between the ADH1 intron and NOS polyadenylation sequences. Thus, pMON19632 is comprised of, from 5' to 3', the enhanced CaMV35S promoter, ADH1 intron, SSU•CTP—GOX coding sequence, and nopaline synthase polyadenylation region in a pUC backbone containing an β-lactamase gene for ampicillin selection in bacteria.

Figure 7A:
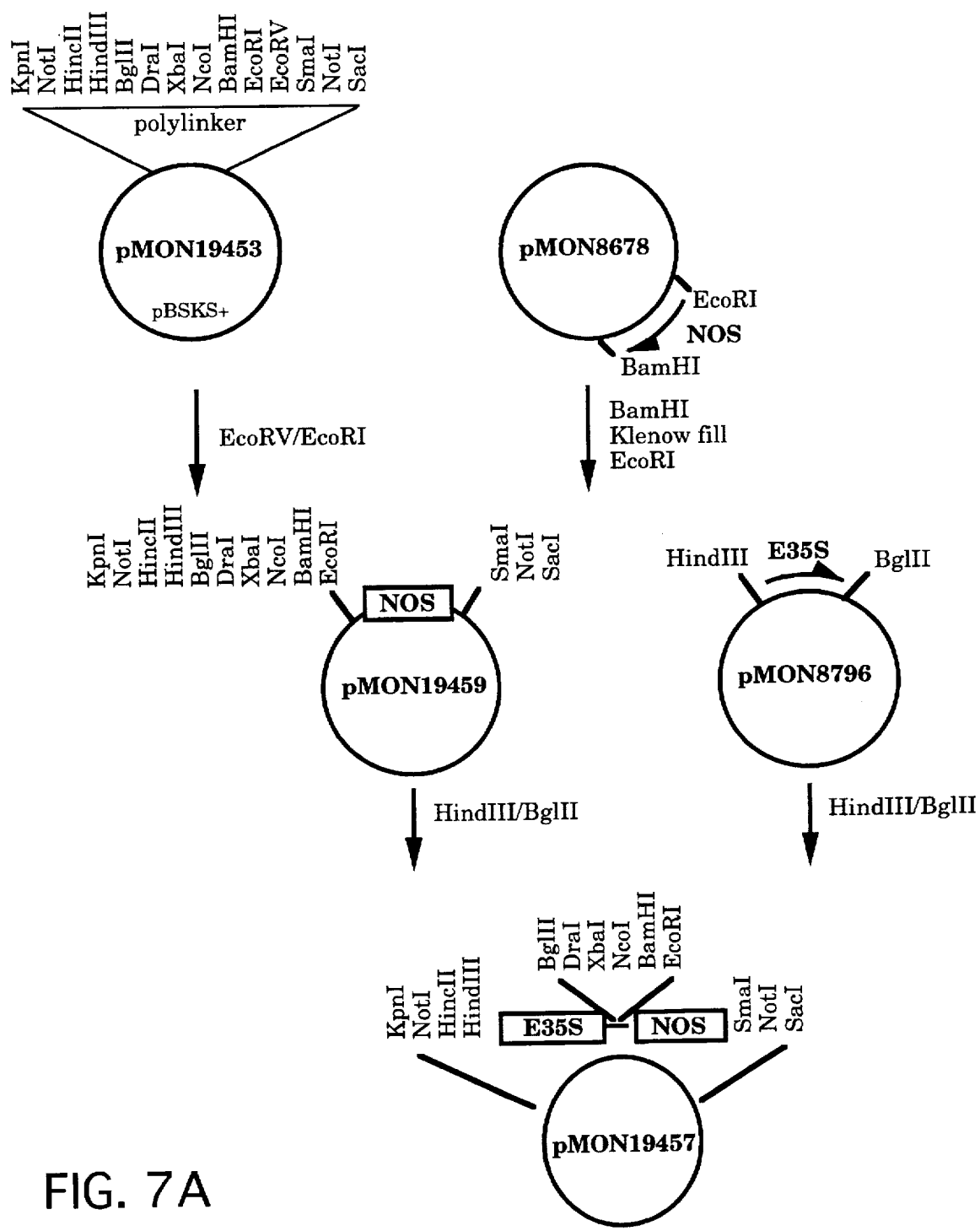
FIGS. 7A and 7B show the steps employed to prepare pMON19433, pMON19457 and pMON19470.
Figure 7B:
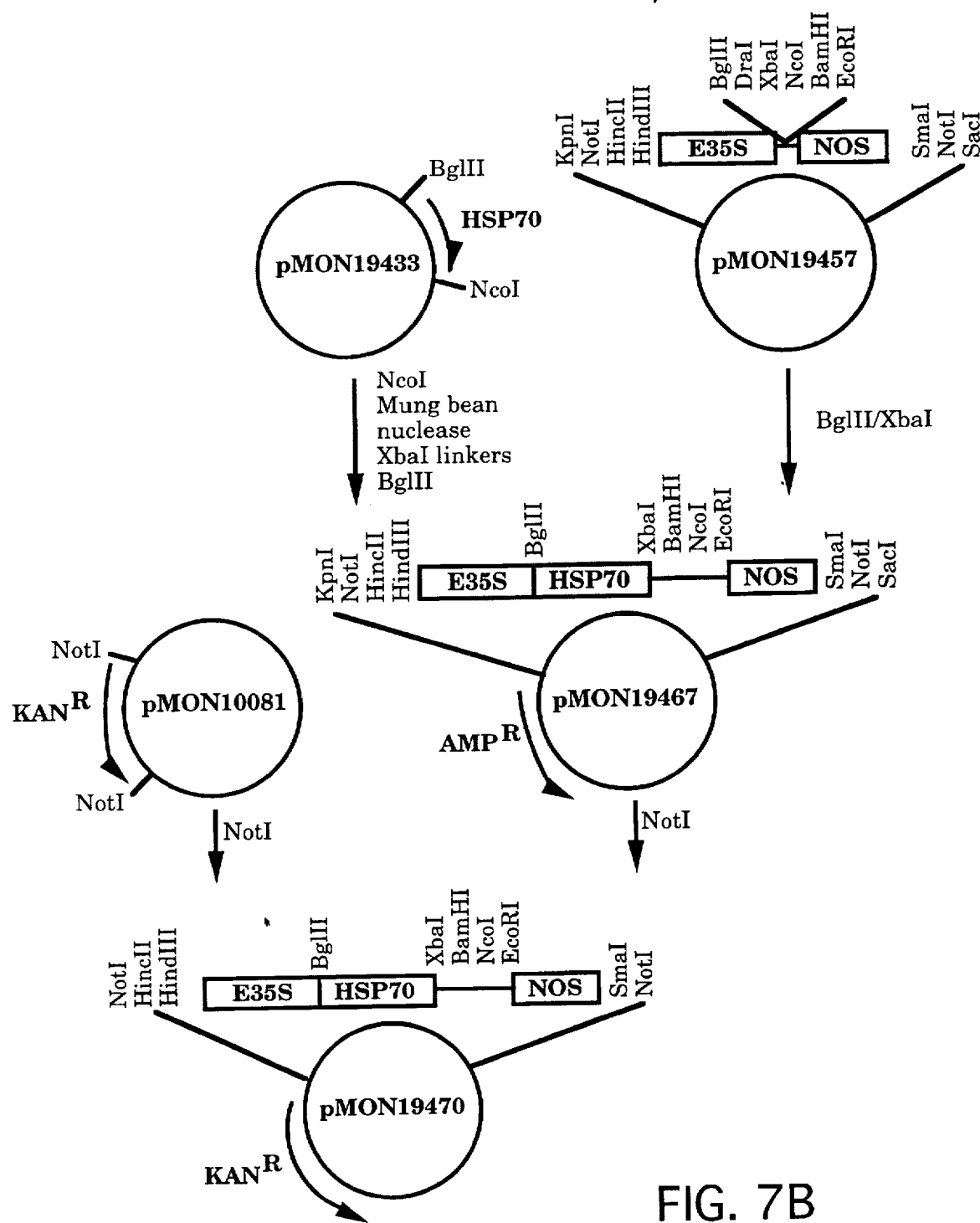
Figure 8:
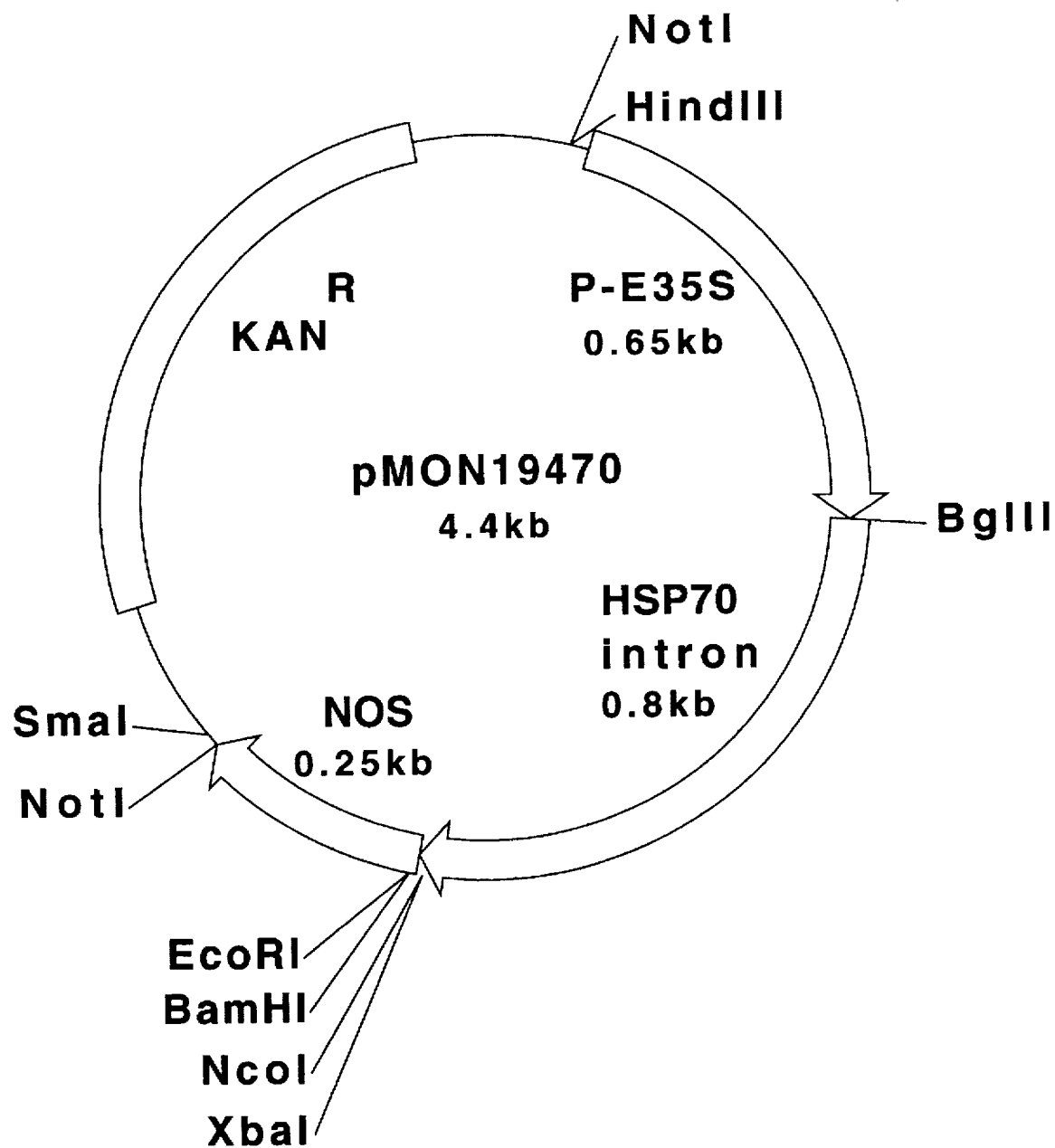
FIG. 8 illustrates a physical map of the plasmid pMON19470 comprising the HSP70 intron and a number of restriction sites for insertion of a structural gene encoding a protein to be expressed in plants.
Figure 17:
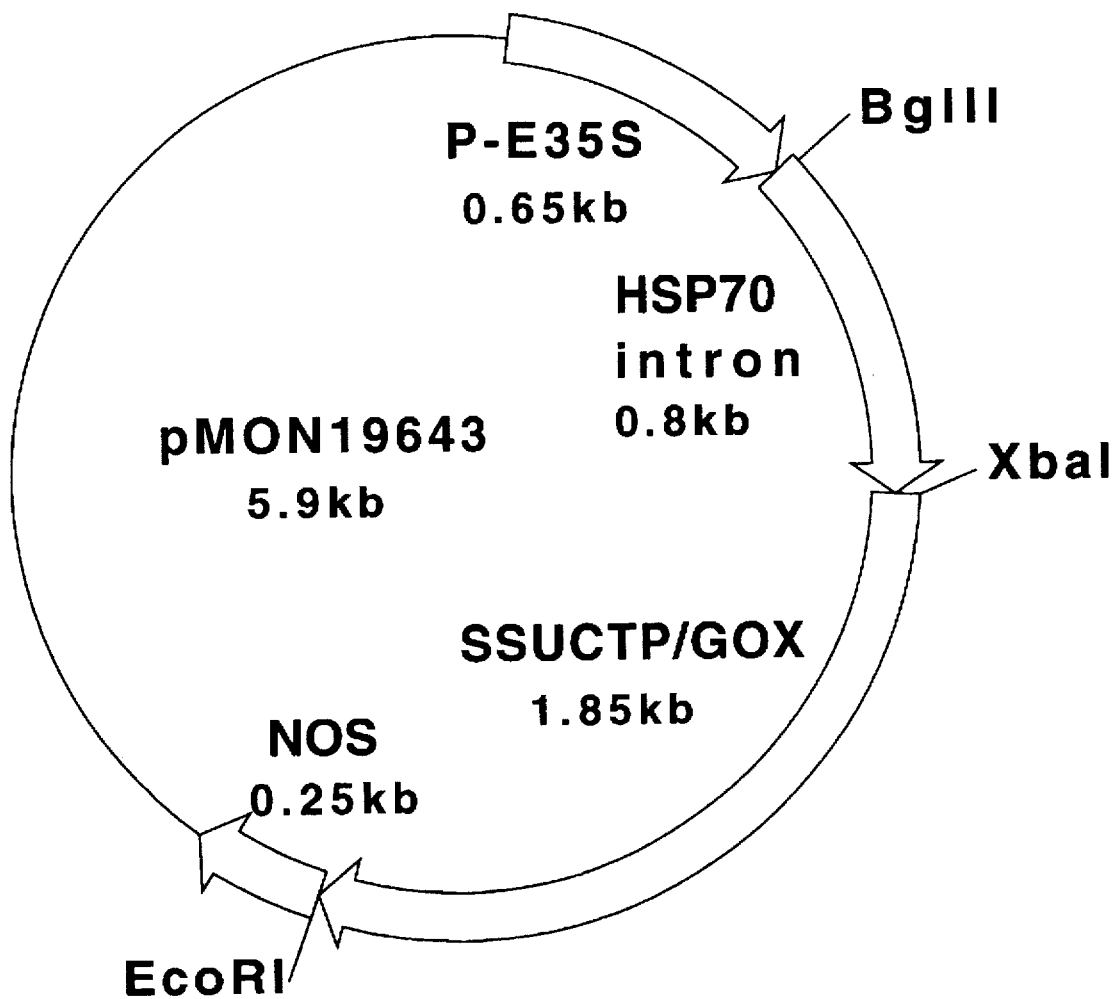
FIG. 17 illustrates a physical map of the plasmid pMON18104 comprising an HSP70 intron and a GOX coding sequence.

A cassette vector pMON19470 was constructed for cloning coding sequences such as GOX adjacent to the HSP70 intron (FIG. 7). A receptor plasmid pMON19453 was made by inserting annealed synthetic oligonucleotides containing the sites KpnI/NotI/HincII/HindIII/BglII/DraI/XbaI/NcoI/BamHI/EcoRI/EcoRV/XmaI/NotI/SacI into pBSKS+ (Stratagene)which had been digested with KpnI and SacI. The nopaline synthase (NOS) polyadenylation region (Fraley et al., 1983, *Proc. Natl. Acad. Sci.* 80:4803–4807) was inserted by digesting pMON8678 (FIG. 5) with BamHI, followed filling Klenow Polymerase to create blunt ends, and digesting with EcoRI. The 0.25 kb NOS fragment was inserted into the polylinker of pMON19453 at the EcoRV/EcoRI sites to form pMON19459. pMON19457 was constructed by inserting a 0.65 kb fragment containing the CaMV E35S promoter (Kay et al., 1987, *Science* 236:1299–1302) into the HindIII/BglII sites in pMON19459. pMON19433 was linearized with NcoI, blunt-ended with mung bean nuclease, and Xba linkers were added. The HSP70 intron fragment was then removed by digestion with BglII and inserted into the XbaI/BglII sites in pMON19457 to form pMON19458. Synthetic linkers to change the order of the restriction sites were then inserted into pMON19458 to form pMON19467. The NotI expression cassette was removed from pMON19467 and inserted into a pUC-like vector pMON10081 which contains the NPTII sequences from pKC7 (Rao and Rogers, 1978, *Gene* 3:247) to form pMON19470 (FIG. 8). Thus, pMON19470 is comprised of, from 5' to 3', the enhanced CaMV35S promoter, HSP70 intron, polylinker for cloning coding sequences, and NOS polyadenylation region in a pUC-like backbone containing an NPTII gene for kanamycin selection in bacteria.

pMON19643 (FIG. 17) was constructed by inserting the SSU•CTP—GOX fusion coding sequences into pMON19470 as a 1.6 kb BglII/EcoRI fragment into BamHI-EcoRI digested pMON19470 (FIG. 8). Thus, pMON19643 is comprised of, from 5' to 3', the enhanced CaMV35S promoter, HSP70 intron, SSU•CTP—GOX coding sequence, and nopaline synthase polyadenylation region in a pUC-like backbone containing an NPTII gene for kanamycin selection in bacteria.

BMS suspension cells were bombarded with pMON19632 or pMON19643 as described in Example 3A. Plasmid EC9 was included in each bombardment so that the transformed BMS cells could be selected on chlorsulfuron. The chlorsulfuron resistant calli were transferred to 5 mm glyphosate medium and moved to fresh 5 mm glyphosate medium after two weeks. After two weeks, the percentage of the calli that survived on the glyphosate medium were scored.

The results are shown in Table 4. The ADH1 intron vector (pMON19632) gave little or no glyphosate resistant calli. The HSP70 intron vector (pMON19643) showed over 40% of the chlorsulfuron resistant calli were also resistant to glyphosate. The levels of GOX protein accumulation in the chlorsulfuron resistant lines were measured by Western blot analysis. As shown in Table 3, the HSP70 intron vector gave demonstrably

TABLE 4

Effect of Introns on GOX Gene Expression in BMS Transformants

| Vector | Intron | % glp resistant | % GOX protein |
|---|---|---|---|
| pMON19632 | ADH1 | 2% | (0.02–0.04%) |
| pMON19643 | HSP70 | 42% | (0.05–0.5%) |

EXAMPLE 6

Effect of HSP70 Intron on EPSP Synthase and Glyphosate Selection

Figure 23:
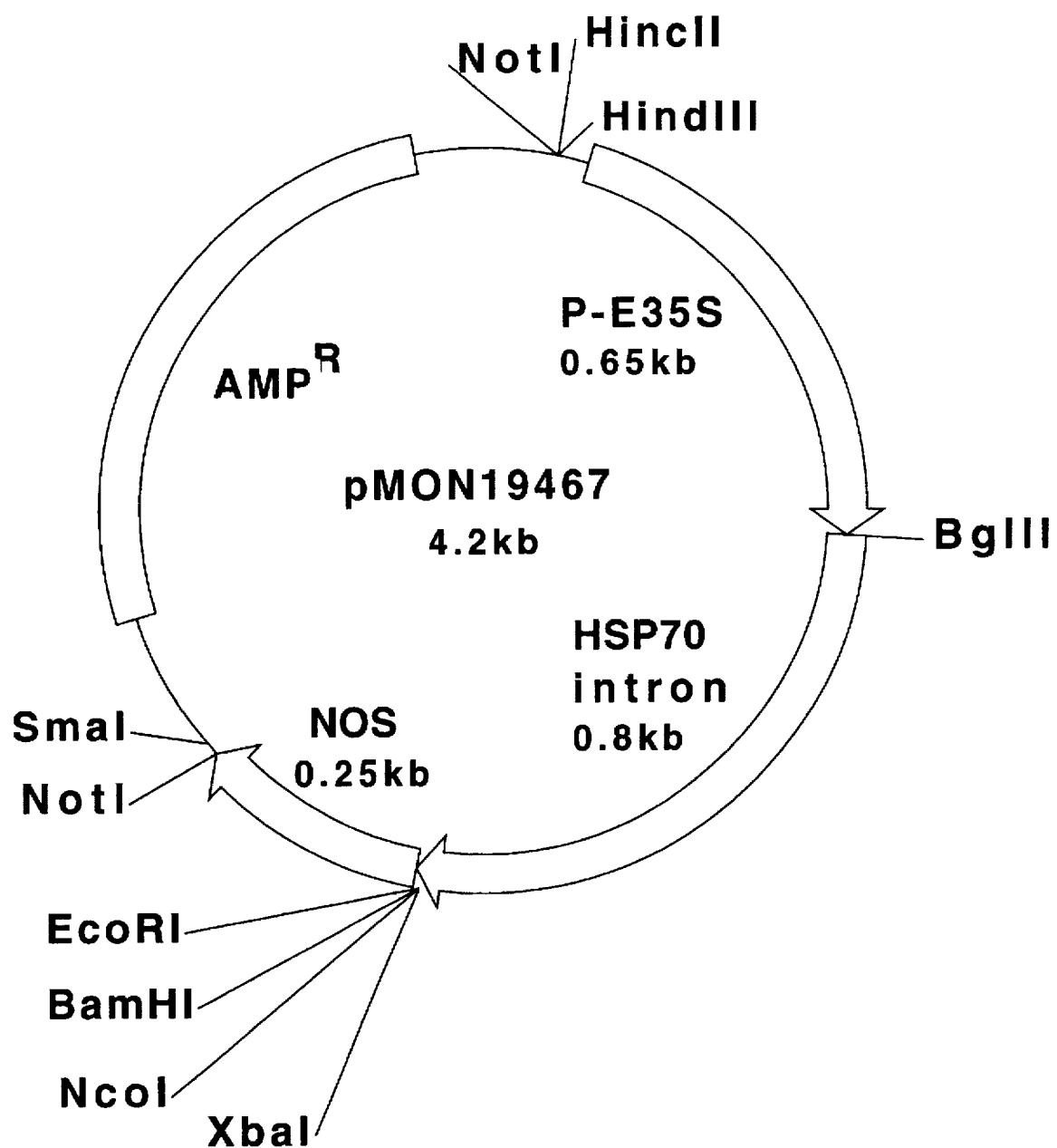
FIG. 23 illustrates a physical map of the cassette plasmid pMON19467 comprising an HSP70 intron.

Two vectors, pMON8631 and pMON19640, were constructed to compare the effects of the ADH1 and HSP70 intron on the expression of the 5-enolpyruvylshikimate-3-phosphate synthase (EPSPS) gene. pMON8631 (FIG. 23) was constructed similarly to pMON8678 (FIG. 5), except that a 1.75 kb fragment containing the maize EPSPS coding sequence with two mutations that confer tolerance the the herbicide glyphosate (Gly101>Ala and Gly163>Asp of mature peptide) was inserted between the ADH1 intron and the NOS polyadenylation sequences. Thus, pMON8631 is comprised of, from 5' to 3', the enhanced CaMV35S promoter, ADH1 intron, EPSPS coding sequence, and nopaline synthase polyadenlyation region in a pUC backbone containing a β-lactamase gene for ampicillin selection in bacteria.

Figure 12:
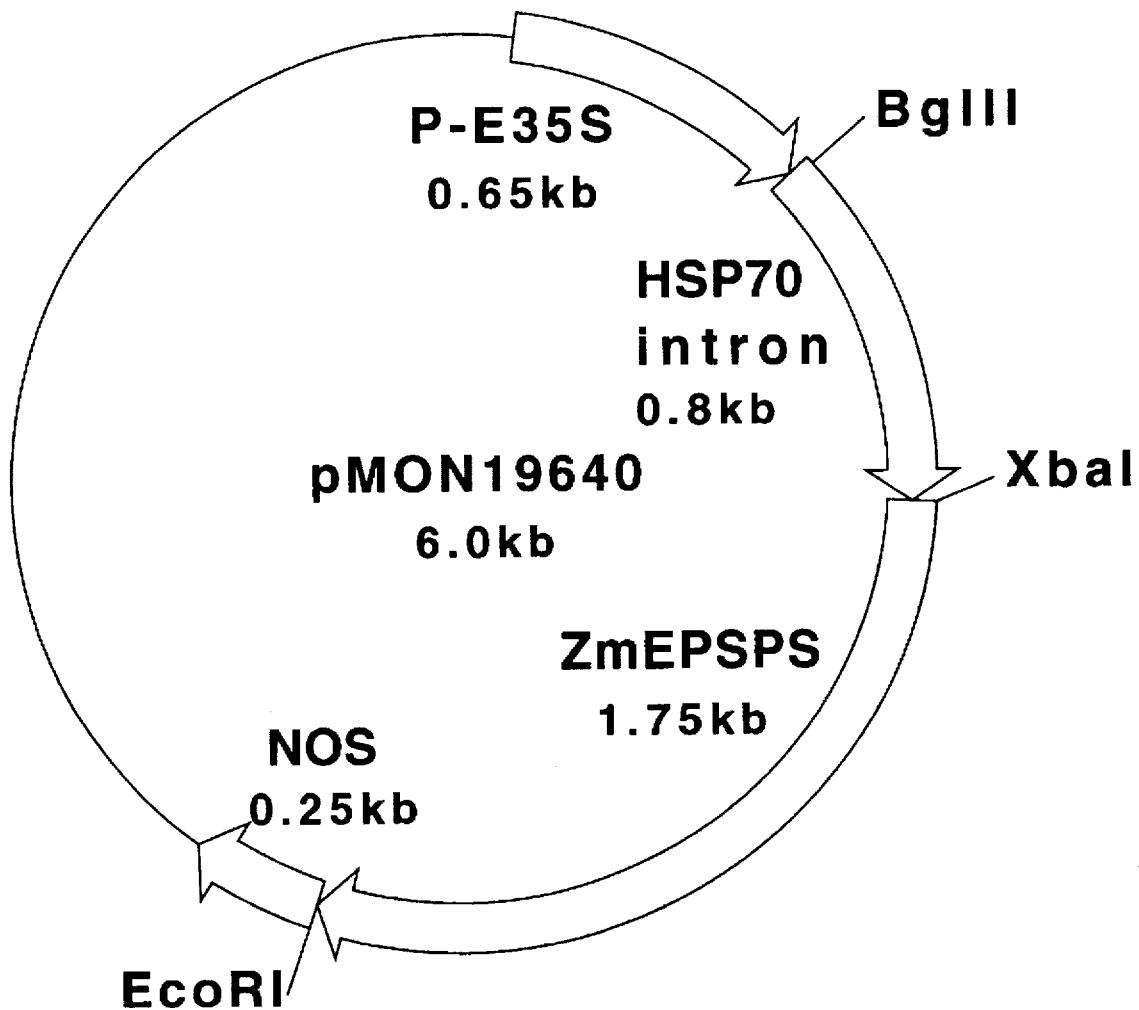
FIG. 12 illustrates a physical map of the plasmid pMON19640 comprising an HSP70 intron and an EPSPS:215 coding sequence.

To form pMON19640 (FIG. 12), the 1.75 kb XbaI-EcoRI fragment from pMON8631 was inserted into the corresponding restriction sites in pMON19470 (FIG. 8). Thus, pMON19640 is comprised of, from 5' to 3', the enhanced CaMV35S promoter, HSP70 intron, EPSPS coding sequence, and nopaline synthase polyadenylation region in a pUC-like backbone containing an NPTII gene for kanamycin selection in bacteria.

Stably transformed BMS lines were produced by direct selection on glyphosate containing medium. Cells were bombarded with either pMON8631 or pMON19640 as in described in Example 3A. After bombardment, the cells were resuspended in MS medium without selection for one day. Glyphosate was then added to the liquid medium to a final concentration of 5 mM, and the cultures incubated for four days. Five days post-bombardment, the cells were embedded in agarose containing 5 mM glyphosate. Approximately 6 weeks after embedding, the number of glyphosate resistant calli were scored. pMON8631 (ADH1 intron) produced 59 glyphosate resistant calli, while pMON19640 (HSP70 intron) produced 117 glyphosate resistant calli, a two fold increase. Although the levels of EPSPS expression in these calli was not quantitated, it is likely that the HSP70 intron vector expresses more EPSPS which in turn results in more transformation events that produce enough EPSPS to overcome the toxic effects of the glyphosate in the medium, thus giving a higher frequency of recovery of glyphosate resistant calli.

EXAMPLE 7

Figure 13:
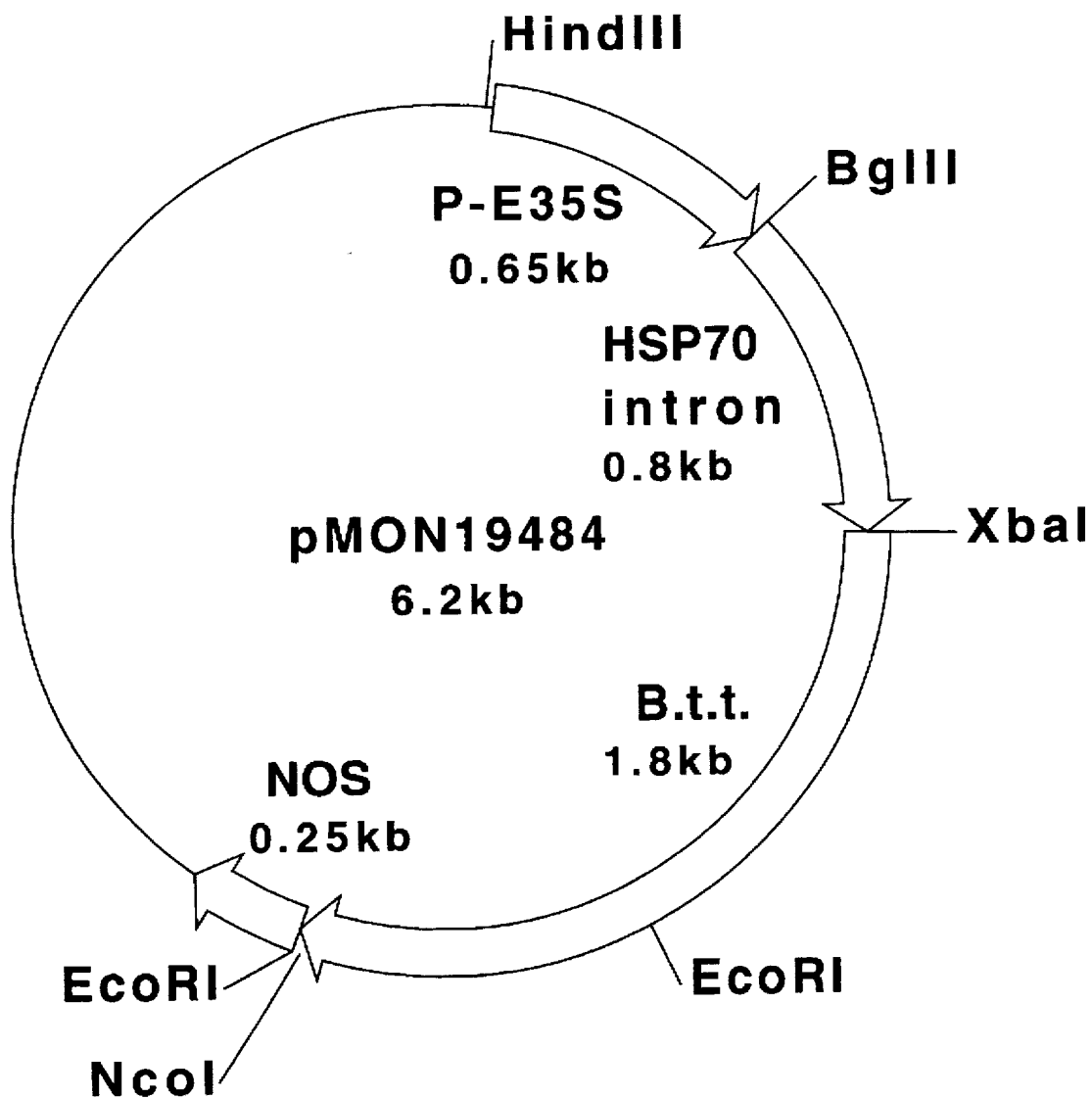
FIG. 13 illustrates a physical map of the plasmid pMON19484 comprising an HSP70 intron and a B.t.t. coding sequence.

Expression g Other Coding, Sequences Using HSP70Intron Vectors Encoding Insecticidal Proteins pMON19484 (FIG. 13) containing a synthetic gene encoding the *Bacillus thuringensis* var. *tenebrionis* (B.t.t.) insecticidal protein (McPherson et al., 1988, *Biofrechnology* 6: 61–66) was constructed by inserting the 1.8 kb B.t.t. gene on a BglII fragment into the BamHI site in pMON19470 (FIG. 8). Thus, pMON19484 is comprised of, from 5' to 3', the enhanced CaMV35S promoter, HSP70 intron, B.t.t. coding sequence, and nopaline synthase polyadenylation region in a pUC-like backbone containing an NPTII gene for kanamycin selection in bacteria.

Stably transformed BMS calli were produced using particle gun bombardment to introduce pMON 19484 as described in Example 3A. pMON19484 was bombarded in combination with EC9 (FIG. 19) into BMS cells. Resistant calli were selected on 20 ppb chlorsulfuron. The resistant calli were then assayed for expression of the B.t.t. gene.

Chlorsulfuron resistant calli bombarded with pMON19484 were screened for expression of the B.t.t. protein utilizing a Colorado Potato Beetle (CPB) feeding assay. CPB larvae were applied to BMS callus which had been blotted slightly to remove excess moisture. Five larvae were allowed to feed on callus representing each chlorsulfuron resistant line. The level of insect mortality and/or stunting was assessed five days later. Forty calli were assayed. Eight calli (20%) showed insecticidal activity, 11 calli (28%) caused stunting, 6 calli (15%) caused small amounts of stunting, and 15 calli (38%) had no effect on the CPB insects.

The calli that showed the greatest insecticidal/stunting effects were analyzed further by Western blot analysis. BMS calli were dried on a Whatman filter and then extracted directly in SDS-PAGE buffer (Laemmli, 1970, Nature 227: 680–685). Levels of total protein were determined (Biorad) and 40–50 ug protein loaded on a 12% SDS-PAGE gel. *E. coli*-produced B.t.t. protein was also loaded as quantitation standards. After gel electrophoresis, proteins were electrophoretically transferred from the gel to membranes (Towbin et al., 1979, *PNAS* 76:4350–4354). The membranes were then incubated with an anti-B.t.t. antibody, followed by detection using a chemiluminescent (Amersham) detection system.

Figure 14:
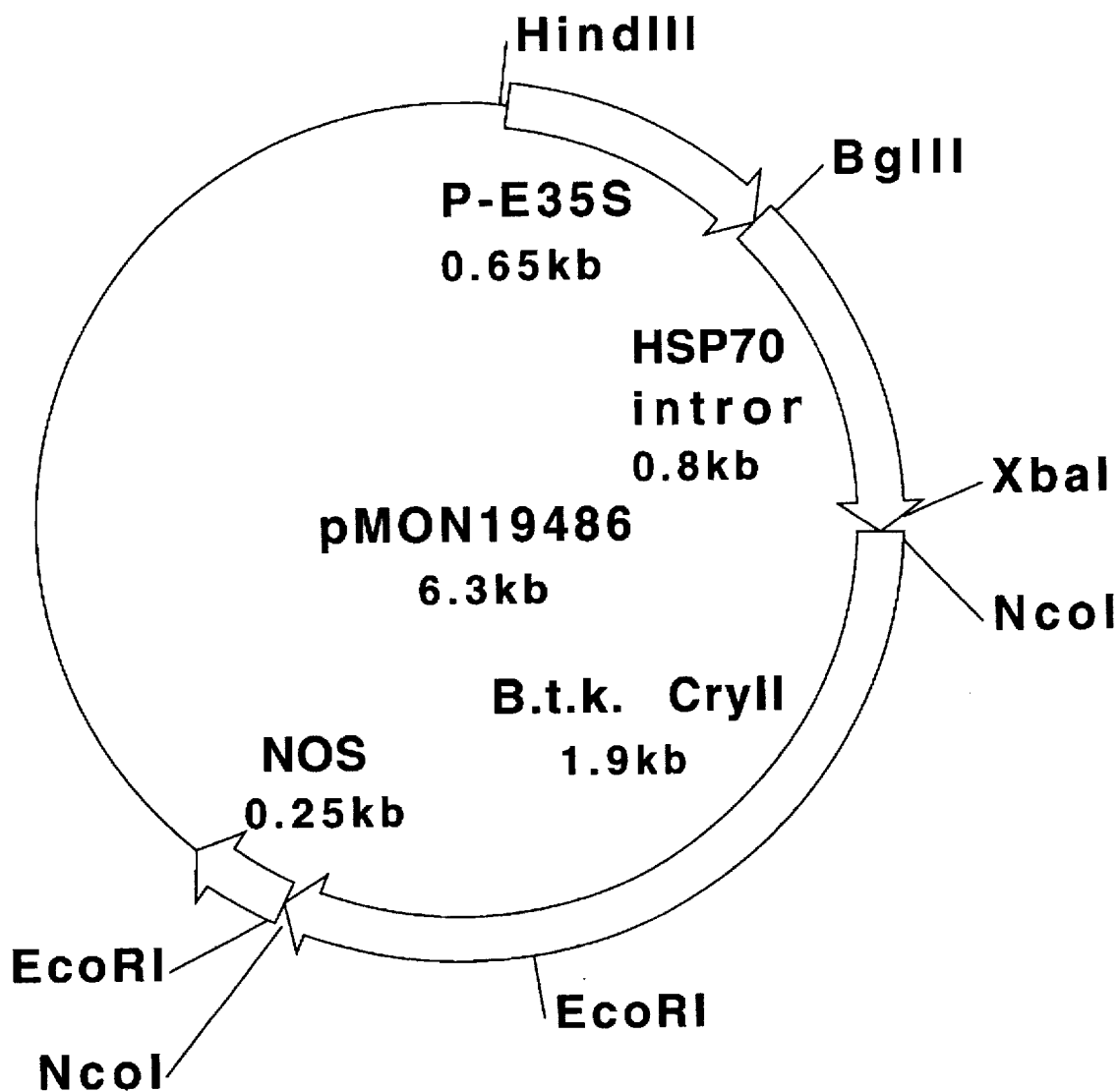
FIG. 14 illustrates a physical map of the plasmid pMON19486 comprising an HSP70 intron and a B.t.k.-P2 CryII coding sequence.

Seven lines were examined. One line showed high levels of protein expression (0.02% total protein), four lines showed moderate B.t.t. protein levels (0.001%), and two lines did not produce enough B.t.t. protein for detection by Western blot.

pMON19486 (FIG. 14) contains a synthetic gene encoding the *Bacillus thuringensis kurstaki* CryIIA gene. The amino acid sequence of this gene (1.9 kb) is identical to the gene referred to as the CryB1 in Widner et al. (1989) *J. Bacteriol.* 171:965–974. It has insecticidal activity against both lepidopteran and dipteran insects. pMON19486 was constructed by inserting the 1.9 kb CryIIA coding sequence on a BglII fragment into the BamHI site in pMON19470 (FIG. 8). Thus, pMON19486 is comprised of, from 5' to 3', the enhanced CaMV35S promoter, HSP70 intron, CryIIA coding sequence, and nopaline synthase polyadenylation region in a pUC-like backbone containing an NPTII gene for kanamycin selection in bacteria.

Stably transformed BMS calli were produced using particle gun bombardment to introduce pMON19486 as described in Example 3A. pMON 19484 was bombarded in combination with EC9 (FIG. 19) into BMS cells. Resistant calli were selected on 20 ppb chlorsulfuron. The resistant calli were then assayed for expression of the CryIIA gene.

Expression of the B.t.k. CryIIA protein in the chlorsulfuron resistant calli bombarded with pMON19486 was initially detected by insecticidal activity in a feeding assay with the sensitive Tobacco Hornworm (THW). Calli with CryIIA expression high enough to kill the THW insects were bulked up and assayed in European Corn Borer (ECB) and Fall Army Worm (FAW) insect feeding assays. Sixteen ECB or 12 FW insects were pre-weighed and then reared on the BMS calli for 7 days. The number of survivors were scored to determine the degree of mortality. The mount of stunting was measured by determining the average weight gain of the surviving insects relative to controls. The data are shown in Table 5.

Calli with insecticidal activity were also assayed for accumulation of the CryIIA protein by Western blot analysis as described above. The amount of CryIIA protein was quantitated relative to E. coli produced standards on the same blot. As shown in Table 5, six of the seven insecticidal lines demonstrated sufficient expression of the CryIIA protein to detect by the less sensitive Western blot. The CryIIA expression ranged from 0.004 to 0.15%, with an average of 0.007%, of total cellular protein.

TABLE 5

Expression of CryIIA in Stable BMS Transformants

| Line | #survivors/initial | | mean weight gain per surviving insect (mg) | | CryIIA protein (%) |
|---|---|---|---|---|---|
| | ECB | FAW | ECB | FAW | |
| control | 10/16 | 10/12 | 3.0 | 3.9 | 0 |
| 12-9 | 0/16 | 10/12 | all dead | 0.5 | 0.004 |
| 3-20 | 2/16 | 11/12 | 0.8 | 1.5 | 0.004 |
| 11-31 | 1/16 | 10/12 | 3.7 | 1.2 | 0.015 |
| 3-4 | 0/16 | 11/12 | all dead | 0.6 | 0.013 |
| 3-10 | 1/16 | 12/12 | 3.5 | 0.8 | 0 |
| 3-38 | 0/16 | 11/12 | all dead | 0.4 | 0.0025 |
| 3-34 | 0/16 | 11/12 | all dead | 0.5 | 0.0025 |

Figure 16:
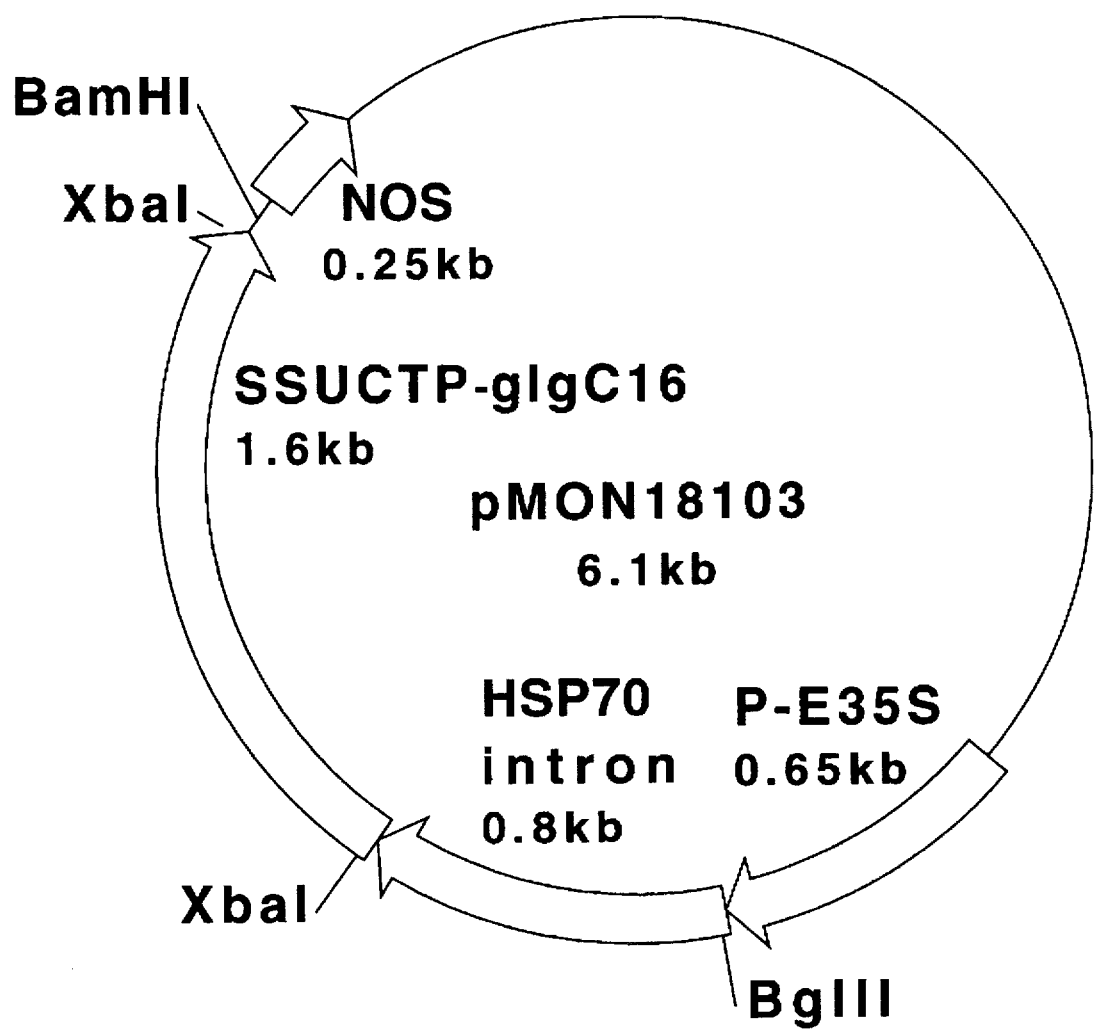
FIG. 16 illustrates a physical map of the plasmid pMON18103 comprising a truncated HSP70 intron and a glgC16 coding sequence.

EXAMPLE 8 pMON18103 (FIG. 16) contains a gene fusion composed of the N-terminal 0.26 Kb chloroplast transit peptide sequence derived from the Arabidopsis thaliana SSU 1a gene (SSU•CTP) (Timko et al., 1988, *The Impact of Chemistry on Biotechnology*, ACS Books, 279–295) and the *E. coli* ADP-glucose pyrophosphorylase mutant gene glgC16 (Leung et al., 1986, *J. Bacterial.* 167: 82–88). Expression of the SSU•CTP/glgC16 fusion results in increased starch accumulation in plant cells. pMON18103 was constructed by inserting the SSU•CTP/glgC16 coding sequence on a 1.6 kb XbaI fragment into the XbaI site in pMON19467 (see FIG. 23). Thus, pMON19486 is comprised of, from 5' to 3', the enhanced CaMV35S promoter, HSP70 intron, SSU•CTP/glgC16 coding sequences, and hopaline synthase polyadenlyation region in a pUC backbone containing a β-lactamase gene for ampicillin selection in bacteria.

Stably transformed BMS calli were produced using particle gun bombardment to introduce pMON18103 as described in Example 3A. pMON19103 was bombarded in combination with EC9 (FIG. 19) into BMS cells. Resistant calli were selected on 20 ppb chlorsulfuron. The resistant calli were then assayed for expression of the glgC16 gene.

Chlorsulfuron resistant BMS lines that had been bombarded with pMON18103 were assayed for starch accumulation using $I_2$/IKI staining (Coe et al., 1988, in *Corn and Corn Improvement*, eds. G. F. Sprague and J. W. Dudley. AGS Inc., Madison, Wis. pp. 81–258). Eight of 67 lines showed increased levels of starch staining relative to control calli. Western blot analyses were performed on these lines as described above. All lines showed ADP-GPP expression, with levels from 0.02–0.1% of total protein relative to quantitation standards using *E. coli*-produced ADP-GPP protein.

Figure 15:
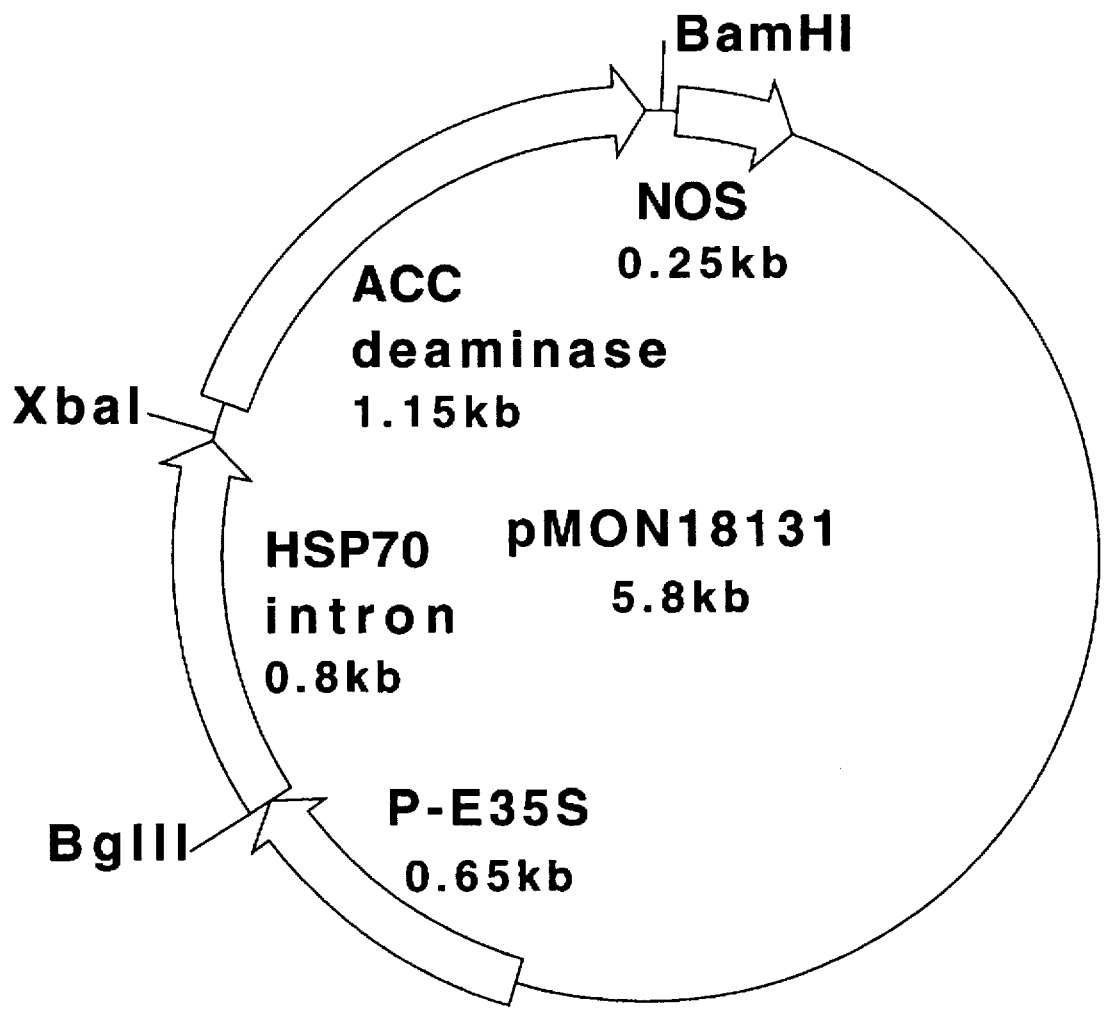
FIG. 15 illustrates a physical map of the plasmid pMON18131 comprising an HSP70 intron and an ACC-deaminase coding sequence.

EXAMPLE 9 pMON18131 (FIG. 15) contains the ACC deaminase gene from Pseudomonas. The ACC deaminase enzyme converts 1-aminocyclopropane-1-carboxylic acid (ACC) to alphaketobutyrate and ammonia (Honma and Shimomura, 1978, *Agric. Biol. Chem.* Vol.42 No.10: 1825–1813). The expression of the ACC deaminase enzyme in plants results in inhibition of the ethylene biosynthesis (Klee et al., 1991, *Plant Cell* Vol. 3, pp. 1187–1193) which affects ripening. pMON18131 was constructed by inserting the 1.1 kb ACC deaminase gene as an XbaI-BamHI fragment into pMON18103 (FIG. 16), replacing the glgC16 coding sequence. Thus, pMON19486 is comprised of, from 5' to 3', the enhanced CaMV35S promoter, HSP70 intron, ACC deaminase coding sequences, and nopaline synthase polyadenylation region in a pUC backbone containing a β-lactamase gene for ampicillin selection in bacteria.

Stably transformed BMS calli were produced using particle gun bombardment to introduce pMON18131 as described in Example 3A. pMON18131 was bombarded in combination with EC9 (FIG. 19) into BMS cells. Resistant calli were selected on 20 ppb chlorsulfuron. The resistant calli were then assayed for expression of the ACC deaminase gene.

Chlorsulfuron resistant calli bombarded with pMON18131 were assayed by Western blot analysis. Seventeen of 24 lines examined showed high levels of ACC deaminase protein accumulation (~0.1% of total protein).

EXAMPLE 10

Figure 24:
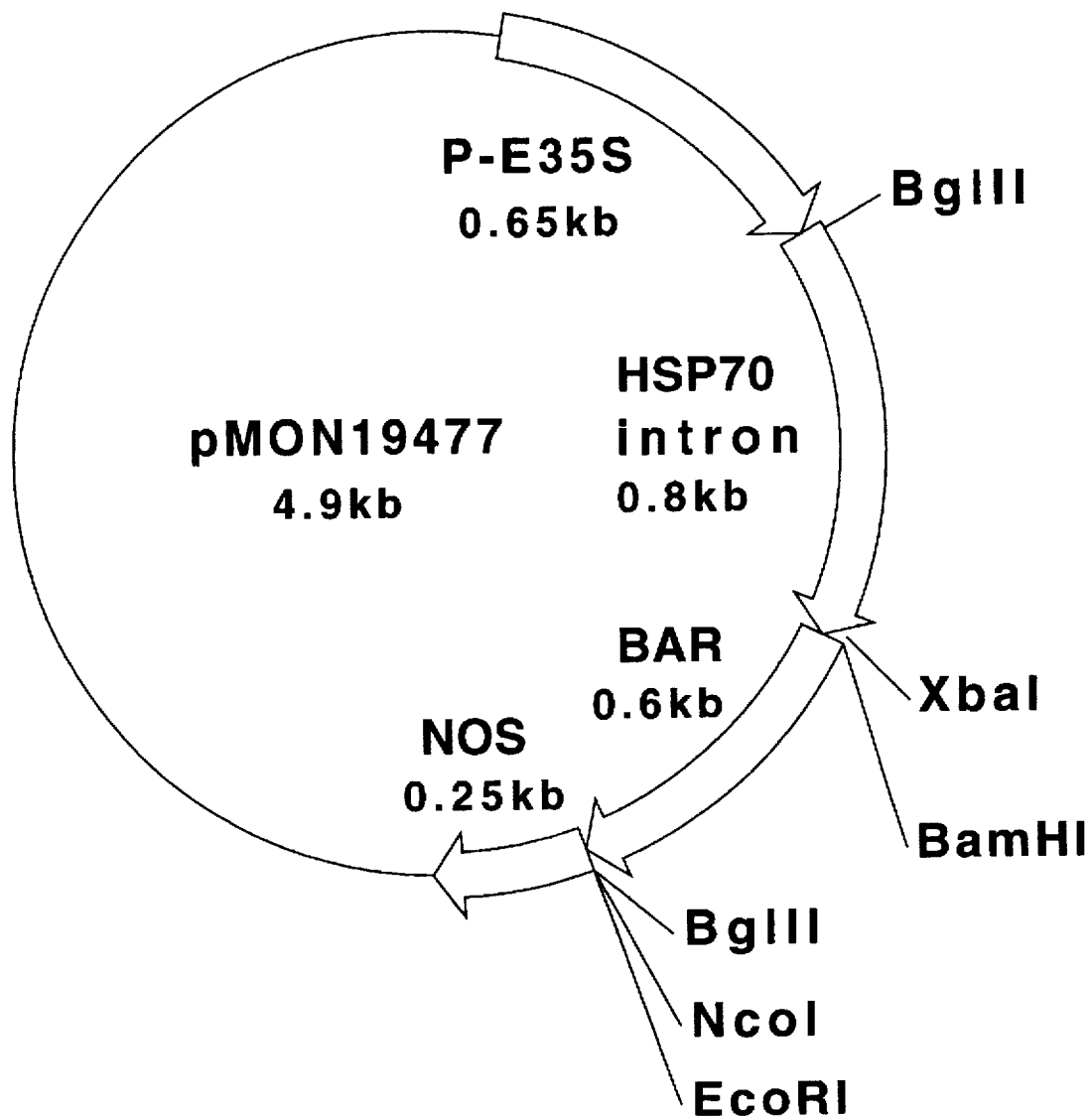
FIG. 24 illustrates a physical map of the plasmid pMON19477 comprising a BAR coding sequence.
Figure 25:
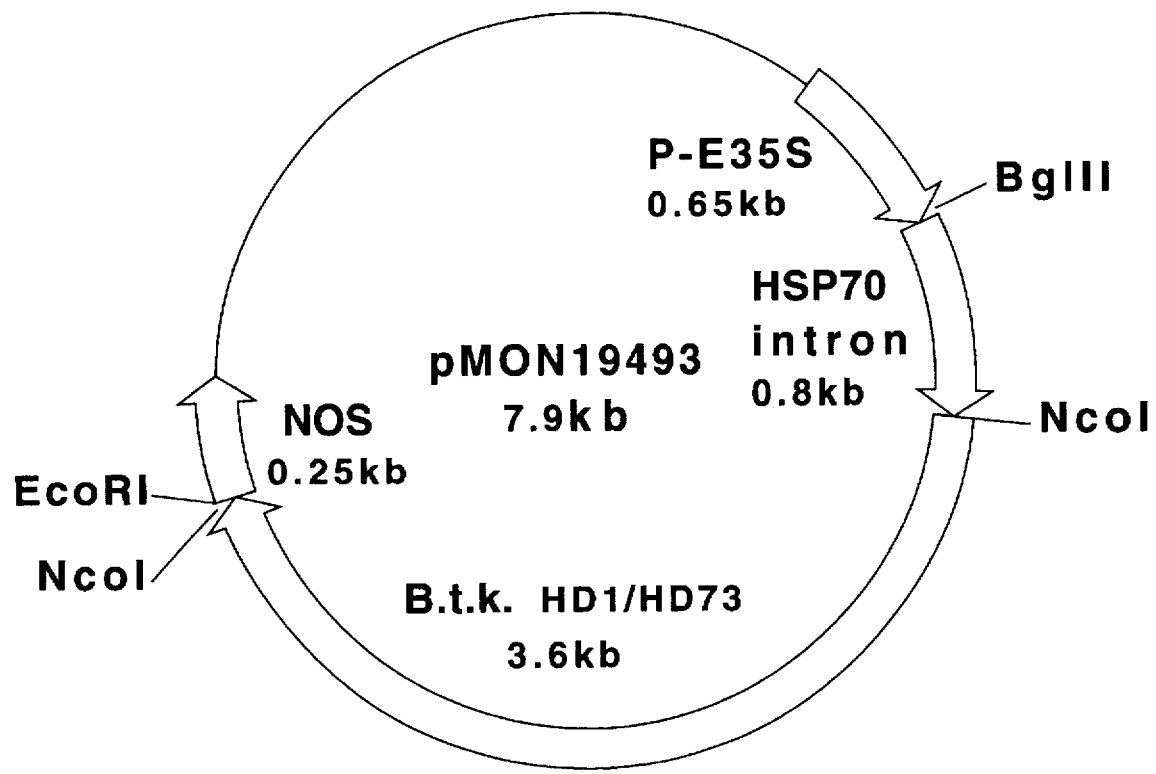
FIG. 25 illustrates a physical map of the plasmid pMON19493 comprising a B.t.k. coding sequence—HD1/HD73 hybrid.
Figure 26:
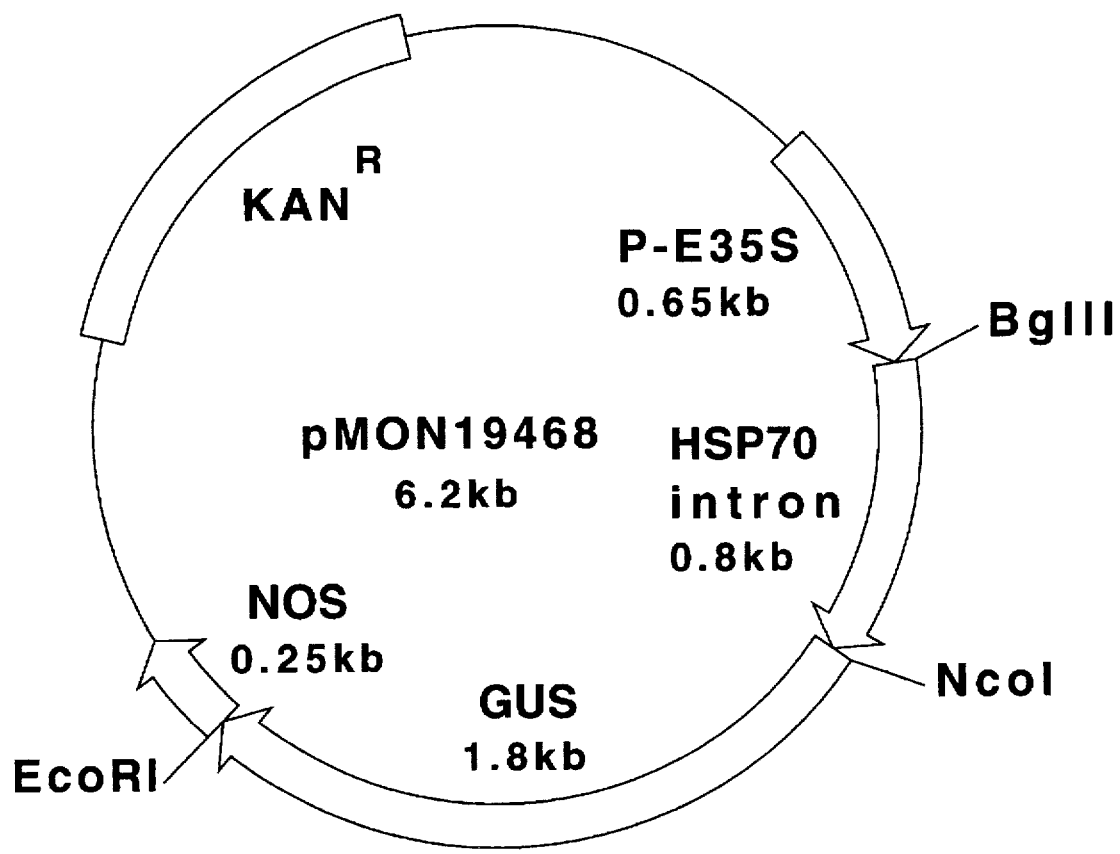
FIG. 26 illustrates a physical map of the plasmid pMON19648 comprising a GUS coding sequence.

Production of Plants Using Vectors Containing the HSP70 Intron and Bialaphos Selection pMON19477 (FIG. 24) contains the BAR gene from *S. hygroscopicus*. The BAR gene encodes a phosphinothricin acetyltransferase enzyme that can be used as a selectable marker by conferring resistance to bialaphos or phosphinothricin, the active ingredient in the herbicide BASTA (Fromm et al., 1990, *Bio/Technology* 8:833–839; De Block et al., 1987, *Embo. J.* 6:2513–2518; Thompson et al., 1987, *Embo. J.* 6:2519–2523). pMON19477 was constructed by inserting the BAR gene as a 0.6 kb BamHI-BClI fragment into the BamHI site in pMON19470 (FIG. 8). Thus, pMON19477 is comprised of, from 5' to 3', the enhanced CaMV35S promoter, HSP70 intron, BAR coding sequence, and nopaline synthase polyadenylation region in a pUC-like backbone containing an NPTII gene for kanamycin selection in bacteria.

pMON19493 (FIG. 25) contains a "synthetic" B.t.k. gene consisting of 1.8 kb truncated gene encoding amino acids 1 to 615 of the *Bacillus thuringensus kurstaki* CryIA(b) insect control protein described by Fischhoff et al. (1987) *Bio/Technology* 5: 807 . 813, translationally fused to the 1.8 kb 3' half of the CryIA(c) gene encoding amino acids 616–1177 (Adang et al. 1985, *Gene* 36: 289–300). Expression of the gene in plants results in insect resistance. pMON19493 was constructed by inserting the 3.6 kb "synthetic" B.t.k. gene coding sequence as a BglII fragment into the BamHI site in pMON19470 (FIG. 8). Thus, pMON19493 is comprised of, from 5' to 3', the enhanced CaM 35S promoter, HSP70 intron, "synthetic" B.t.k. coding sequence, and nopaline synthase polyadenylation region in a pUC-like backbone containing an NPTII gene for kanamycin selection in bacteria.

pMON19468 (FIG. 26) contains the E. coli GUS gene and can be used as a visible scoreable marker of transformation using histochemical staining. pMON19468 was constructed using the 1.8 kb BglII-EcoRI fragment containing the GUS gene from pMON8678 inserted into the BamHI-EcoRI site in the pMON19470 backbone. Thus, pMON19468 is comprised of, from 5' to 3', the enhanced CaMV35S promoter, HSP70 intron, GUS coding sequence, and nopaline synthase polyadenylation region in a pUC-like backbone containing an NPTII gene for kanamycin selection in bacteria.

Embryogenic cultures were initiated from immature maize embryos of the "Hi-Ir" genotype (Armstrong et al., 1991, *Maize Genetic Newsletter* 65:92–93) cultured 18–33 days on N6 2-100-25-Ag medium (Chu et al., 1975, *Sci. Sin. Peking* 18:659–688) modified to contain 2 mg/L 2,4-dichlorophenoxyacetic acid, 180 mg/L casein hydrolysate, 25 mm L-proline, 10 uM silver nitrate, pH5.8, solidified with 0.2% PhytagelTM (Sigma). These embryogenic cultures were used as target tissue for transformation by particle gun bombardment.

A 2:1:1 mixture of pMON19477, pMON19493, and pMON19468 plasmid DNAs was precipitated onto tungsten M10 particles by adding 12.5 ul of particles (25 mg/ml in 50% glycerol), 2.5 ul experimental plasmid DNA (1 ug/ul), 12.5 ul 1M calcium chloride, and 5 ul 0.1M spermidine, and vortexing briefly. The particles were allowed to settle for 20 minutes, after which 12.5 ul of supernatant was removed and discarded. Each sample of DNA-tungsten was sonicated briefly and 2.5 ul was bombarded into the embryogenic cultures using a PDS-1000 Biolisitics particle gun (DuPont).

The tissue was transferred to fresh, nonselective medium the day after bombardment. Six days post-bombardment, the material was transferred to selective media containing 2 mg/L 2,4-dichlorophenoxyacetic acid, 10 uM silver nitrate, no casamino acids or proline, and 0.3 mg/L bialaphos. After 2–3 weeks, the cultures were transferred to fresh media which contained 1.0 mg/L bialaphos. The cultures were maintained on the 1.0 mg/L bialaphos media, transferred at 2–3 week intervals, until bialaphos-resistant calli could be distinguished. Seven bialaphos resistant calli were recovered from eight plates of embryogenic material.

Bialaphos resistant lines were bulked up and assayed for B.t.k. or GUS expression. All lines were tested for insecticidal activity in Tobacco Hornworm (THW) feeding assays to test for B.t.k. expression. Approximately 0.5 g of the embryogenic callus was fed to 10–12 THW larvae. Two lines, 284-5-31 and 284-6-41, were positive and showed significant lethality to the THW insects, indicating that the B.t.k. gene from pMON19493 had integrated into their genomes and was being expressed. All lines were also assayed for GUS expression using a histochemical assay (Jefferson, R. A., Kavanagh, T. A., and Bevan, M. W., 1987, *Embo. J.* 6:3901–3907). Of the seven lines tested, only a single line, 284-8-31, showed any detectable blue staining indicative of GUS expression from pMON 19468.

Plants were regenerated from all of the bialophos resistant calli in a three step regeneration protocol. All regeneration was performed on 1 mg/L BASTA. Embryogenic tissue was incubated on each medium for about two weeks and then transferred to the medium for the next step (see Table 6 for regeneration media ingredients). The first two steps were carded out in the dark at 28° C., and the finalstep under a 16:8 hour photoperiod, ~70 uE m-2 sec-1 provided by cool-white fluorescent bulbs, at ~25° C. Small green shoots that formed on Regeneration Medium 3 in 100×25 mm Petri plates are transferred to Regeneration Medium 3 in 200×25 mm PyrexTM or PhytatraysTM to permit further plantlet development and root formation. Upon formation of a sufficient root system, the plants were carefully removed from the medium, the root system washed under running water, and the plants placed into 2.5" pots containing Metromix 350 growing medium. The plants were maintained for several days in a high humidity environment, and then the humidity was gradually reduced to harden off the plants. The plants were transplanted from the 2.5" pots to 6" pots and finally to 10" pots during growth.

TABLE 6

| Regen 1 | Regen 2 | Regen 3 |
|---|---|---|
| MS salts (Sigma; 4.4 g/L | N6 salts (Sigma; 4.0 g/L | MS salts (Sigma; 4.4 g/L |
| 1.30 mg/L nicotinic acid | 0.5 mg/L nicotinic acid | 1.30 mg/L nicotinic acid |
| 0.25 mg/L pyridoxine HCl | 0.5 mg/L pyridoxine HCl | 0.25 mg/L pyridoxine HCl |
| 0.25 mg/L thiamine HCl | 1.0 mg/L thiamine HCl | 0.25 mg/L thiamine Hl |
| 0.25 mg/L Ca-pantothenate | 2.0 mg/L glycine | 0.25 mg/L Ca-pantothenate |
| 100 mg/L myo-insitol | 60 g/L sucrose | 100 mg/L myo-inositol |
| 1 mM asparagine | 2.0 g/L Phytagel ™ | 1 mM asparagine |
| 0.1 mg/L 2,4-D | pH 5.8 | 20 g/L sucrose |
| 0.1 µM ABA |  | 2.0 g/L Phytagel ™ |
| 20 g/L sucrose |  | pH 5.8 |
| 2.0 g/L Phytagel ™ |  |  |
| pH 5.8 |  |  |

All corn plants regenerated from bialaphos resistant embryogenic calli were shown to express at least one of the genes that had been bombarded: BAR, B.t.k., or GUS. Plants regenerated from the bialophos resistant, THW negative callus lines were confirmed to be transgenic and expressing the BAR gene by BASTA leaf painting assays. Seedlings were assayed when 4–5 leaves had fully emerged from the whorl. A solution of 1% BASTA, 0.1% Tween20 was applied to the upper and lower surfaces of the first fully emerged leaf. The plants were scored three days after painting. The control plants showed yellowing and necrosis on the leaves, while the leaves from the resistant lines were green and healthy. This indicates not only that the BAR gene in pMON19477 was expressed in these plants, but also that the expression levels were high enough to confer resistance to the herbicide BASTA at the plant level.

Plants regenerated from the two lines that had shown THW activity, 284-5-31 and 284-6-41, were assayed for B.t.k. expression by whole plant feeding assays. Plants approximately 30" in height were inoculated with 100 European Corn Borer (ECB) eggs. Feeding damage was scored on a scale of 0 (no damage) to 9 (high level of leaf feeding damage) two weeks after inoculation. The control plants scored insect feeding ratings of 9. All plants from either line containing pMON19493 received ratings of zero; no ECB damage was present.

The ECB feeding studies indicate that the B.t.k. gene was expressed at high enough levels in the regenerated plants to impart insect resistance. To quantitate the level of expression, samples from the regenerated lines were assayed by ELISA. Eight plants regenerated from each callus line were analyzed. Plants from line 284-5-31 ranged in B.t.k. expression from 0.006 to 0.034% of total cellular protein, with an average value of 0.02%. Plants from line 284-6-41 ranged in B.t.k. expression from 0.005 to 0.05%, also with an average of 0.02% of total protein.

EXAMPLE 11

Production of Plants Using Glyphosate Selection Vectors Containing the HSP70 Intron pMON19640 (FIG. 12) contains a 5-enolpyruvyl-shikimate-3-phosphate synthase (EPSPS) gene. To form pMON19640 (FIG. 12), a 1.75 kb XbaI-EcoRI fragment containing the maize EPSPS coding sequence with two mutations (Gly144>Ala and Gly206>Asp) of mature peptide that confers tolerance to glyphosate herbicide was inserted into the corresponding restriction sites in pMON19470 (FIG. 8). Thus, pMON19640 is comprised of, from 5' to 3', the enhanced CaMV35S promoter, HSP70 intron, EPSPS coding sequence, and nopaline synthase polyadenylation region in a pUC-like backbone containing an NPTII gene for kanamycin selection in bacteria.

pMON19643 (FIG. 17) contains a gene fusion composed of the N-terminal 0.26 Kb chloroplast transit peptide sequence derived from the *Arabidopsis thaliana* SSU 1a gene (SSU CTP) (Timko et al., 1988, *The Impact of Chemistry on Biotechnology*, ACS Books, 279–295) and the C-terminal 1.3 Kb synthetic GOX gene sequence. The COX gene encodes the enzyme glyphosate oxidoreductase which catalyzes the conversion of glyphosate to herbicidally inactive products, aminomethylphosphonate and glyoxylate. Plant expression of the gene fusion produces a pre-protein which is rapidly imported into chloroplasts where the CTP is cleaved and degraded releasing the mature GOX protein (della-Cioppa et al., 1986, *Proc. Natl. Acad. Sci. U.S.A.* 83: 6873–6877). pMON19643 (FIG. 18) was constructed by inserting the SSU•CTP—GOX fusion coding sequences into pMON19470 as a 1.6 kb BglII/EcoRI fragment into BamHI-EcoRI digested pMON19470 (FIG. 8). Thus, pMON19643 is comprised of, the from 5' to 3', enhanced CaMV35S promoter, HSP70 intron, SSU•CTP—GOX coding sequence, and nopaline synthase polyadenylation region in a pUG-like backbone containing an NPTII gene for kanamycin selection in bacteria.

Embryogenic cultures were initiated from immature maize embryos of the "Hi-Ir" genotype (Armstrong et al., 1991, *Maize Genetic Newsletter* 65:92–93) cultured 18–33 days on N6 1-100-25 medium (Chu et al., 1975, *Sci. Sin. Peking*, 18:659–688) modified to contain 1 mg/L 2,4-dichlorophenoxyacetic acid, 180 mg/L casein hydrolysate, 25 mM L-proline, and solidified with 0.2% Phytagel™ (Sigma). These embryogenic cultures were used as target tissue for transformation by particle gun bombardment.

A 1:1 mixture of pMON19640 and pMON19643 plasmid DNAs was precipitated onto tungsten M10 particles by adding 12.5 ul of particles (25 mg/ml in 50% glycerol), 2.5 ul experimental plasmid DNA (1 ug/ul), 12.5 ul 1M calcium chloride, and 5 ul 0.1M spermidine, and vortexing briefly. The particles were allowed to settle for 20 minutes, after which 12.5 ul of supernatant was removed and discarded. Each sample of DNA-tungsten was sonicated briefly and 2.5 ul was bombarded into the embryogenic cultures using a PDS-1000 Biolistics particle gun (DuPont).

One week after bombardment, cultures were transferred to fresh N6 1-0-25 medium (same as the initiation medium, except removing casein hydrolysate and adding 1 mM glyphosate). After two weeks growth on 1 mM glyphosate medium, cultures were transferred to the same base medium but with 3 mm glyphosate. Additional transfers were made at approximately 2 week intervals on 3 mM glyphosate medium. Glyphosate resistant calli were identified approximately 8–10 weeks post-bombardment, at a frequency of approximately 0.2–1.0 resistant calli per bombarded plate.

Plants were regenerated from glyphosate resistant calli as described for bialaphos resistant calli in Example 10, except that instead of 1 mg/L Basta either 0.01 mm glyphosate or no selective agents were added to the culture medium. Plants were analyzed for expression of pMON19643 by Western blot analysis. Leaf punches were taken from several individual plants regenerated from three independent glyphosate resistant calli. All three lines showed detectable levels of GOX gene expression. Four plants assayed from line 264-2-1 had a low but detectable level of GOX expression (approximately 0.002% of total protein). Five plants from line 269-1-1 showed higher GOX protein levels ranging from 0.04–0.06% of total protein. Lastly, 23 plants were assayed from line 292-5-1. GOX protein levels ranged from 0.05 to 0.1% of total protein. These plants sprayed with glyphosate at 29 oz./acre produced fully fertile plants. $R_1$ progeny of these plants were sprayed with glyphosate at 29, 58 and 115 oz/acre. One line of plants showed no vegetative damage at the highest application rate indicating glyphosate resistance at levels at which complete weed control would be achieved.

EXAMPLE 12

Effect of the HSP70 Intron Alterations

A. Deletions within the HSP70 intron.

Figure 3:
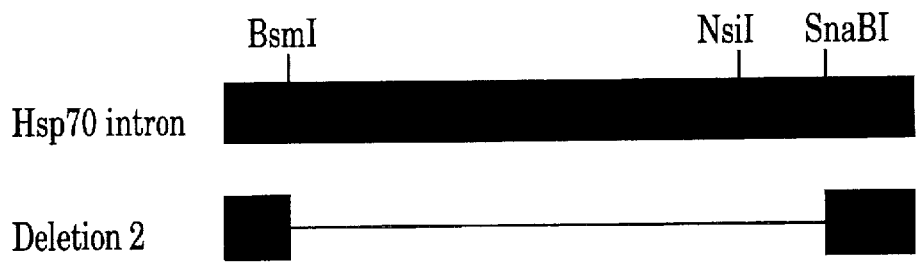
FIG. 3 illustrates another truncated DNA sequence with internal deletions of the intron from the 70 Kd maize heat shock protein, SEQ ID NO:3.

Deletion 1 (FIG. 2) (SEQ ID NO:2) was created by digestion of pMON19433 with BsmI and NsiI, followed by treatment with T4 polymerase to create blunt ends, and religation. Deletion 2 (FIG. 3) (SEQ ID NO:3) was made similarly, except using digestion with BsmI and SnaBI. The effect on gene expression of the full length HSP70 intron versus the effect of Deletion 1 or Deletion 2 was compared in BMS particle gun transient assays as described in Example 2. As shown below, the introns with internal deletions increase GUS gene expression over the no intron control to a similar extent as the full length intron in pMON 19433.

| Intron | Relative GUS Expression |
| --- | --- |
| none | 1X |
| HSP70 full length | 32–51X |
| HSP70 deletion 1 | 14–38X |
| HSP70 deletion 2 | 14–30X |

B. Alterations in 5' and 3' slice site consensus sequences.

In the original polymerase chain reaction (PCR) synthesis of the HSP70 intron by polymerase chain reaction, a variant intron was also synthesized. This variant intron, when cloned adjacent to β-glucuronidase or luciferase, increases expression 4 fold relative to a no intron control but 10 fold less than the wild type HSP70 intron. The only significant difference in nucleotide sequence from that shown in SEQ ID NO:1 was a deletion of the adenine at nucleotide 19.

The HSP70 intron differs from the published (Brown, J. W. S., 1986, *Nuc. Acid Res.* 14:9949–9959) 5' splice site consensus sequence at two positions and from the 3' splice site consensus sequence at one position. The deletion of nucleotide 19 causes the variant HSP70 intron to diverge from the 5' splice site consensus sequence at four positions. Thus, the variant intron probably does not splice as efficiently as the wildtype intron and this may account for the difference in their effect on gene expression.

To address this question, variants of the HSP70 intron that contain perfect consensus sequences at the 5' splice junction, 3' splice junction, or both were constructed. The variants of the HSP70 intron were synthesized by PCR utilizing primers containing the desired changes to mutate the HSP70 intron splice sites to the 5' and/or 3' splice junction consensus sequences. Specifically, the 5' splice junction consensus primer contained nucleotides 1 to 26 of SEQ ID NO:1 except that nucleotide 15 and nucleotide 20 were each changed to adenine. The 3' splice junction consensus primer contained nucleotides that complement nucleotides 791 to 816, except that nucleotide 800 was changed to a guanine (cytosine in the primer).

The PCR products containing the variant HSP70 introns were digested with BglII and NcoI and cloned into pMON8677, analogously to the construction of pMON19433. Therefore, each vector contains, from 5' to 3', the enhanced CaMV35S promoter, HSP70 intron (original or variant), β-glucuronidase (GUS) coding sequence, and nopaline synthase polyadenylation region. They are all identical except for the intron. pMON19433 contains the original HSP70 intron, pMON19460 contains the 5' splice site consensus variant intron, pMON19463 contains the 3' splice site consensus variant intron, and pMON19464 contains a variant intron containing both 5' and 3' splice site consensus sequences.

pMON19460, pMON19463, pMON19464, and pMON19433 were compared in transient gene expression assays in BMS cells as described in Example 2. As shown below, none of the variations in the HSP70 intron significantly altered GUS gene expression.

| Vector | Splice junction | | Relative GUS expression |
| --- | --- | --- | --- |
| | 5' | 3' | |
| pMON19433 | HSP70 wt | HSP70 wt | 1X |
| pMON19460 | consensus | HSP70 wt | 1.1–1.4X |
| pMON19463 | HSP70 wt | consensus | 1.1–1.4X |
| pMON19464 | consensus | consensus | 1.6–1.7X |

C. Increasing the n-tuber of exon sequences does not effect the HSP70 intron.

The original HSP70 "intron" contains the entire intervening sequence as well as 10 bases of exon 1 and 11 bases of exon 2. Because the intron is placed in the 5' untranslated leader region between the enhanced CaMV35S promoter and coding sequence, those 21 bases of exon sequence are left behind in the leader. PCR primers that give 50 nucleotides of the 3' end of liSP70 exon 1 and/or 28 nucleotides of the 5' end of HSP70 exon 2 (Shah et al., 1985, In *Cell and Mol. Biol. of Plant Stress*. Alan R. Liss, Inc. pp.181–200) were used to synthesize introns containing different amounts of exon sequences to determine if extra HSP70 exon sequences would affect the splicing efficiency and ability to increase gene expression.

The PCR products containing the various HSP70 introns with different exon lengths were digested with BglII and NcoI and cloned into pMON8677, analogously to the construction of pMON19433. Therefore, each vector contains, from 5' to 3', the enhanced CaMV35S promoter, HSP70 intron plus surrounding exon sequences, β-glucuronidase (GUS) coding sequence, and nopaline synthase polyadenylation region. They are all identical except for the length of the HSP70 exon surrounding the intron.

These vectors were then compared in transient gene expression assays in BMS cells as described in Example 2. As shown below, none of the variations in the HSP70 intron significantly altered GUS gene expression.

| Vector | Exon 1 | Exon 2 | Relative GUS Expression |
| --- | --- | --- | --- |
| 19433 | 10nt | 11nt | 1X |
| 19462 | 10nt | 28nt | 0.6–0.9X |
| 19465 | 50nt | 11nt | 1.2–1.5X |
| 19466 | 50nt | 28nt | 0.8–1.5X |

EXAMPLE 13

HSP70 Intron Increases Gene Expression in Wheat Cells

To test the effect of introns on gene expression in wheat cells, transient gene expression assays were performed. C983 wheat suspension cells (obtained from Dr. I. Vasil, Univ. of Florida) were plated and bombarded with β-glucuronidase vectors containing no intron (pMON8677), ADH1 intron (pMON8678), and the HSP70 intron (pMON19433) as described for corn suspension cells in Example 2. As shown below, the effect of the ADH1 and HSP70 introns on GUS expression in wheat cells is comparable to that in corn cells. The ADH1 intron vector produces higher levels of GUS expression expression than does the vector with no intron, but the HSP70 intron vector produces significantly higher levels of expression than the ADH1 intron vector.

| Vector | Intron | Mean Relative GUS |
| --- | --- | --- |
| pMON8677 | none | 1X |
| pMON8678 | ADH1 | 2X |
| pMON19433 | HSP70 | 6–9X |

EXAMPLE 14

The HSP70 Intron Increases Gene Expression in Rice

Rice tissue culture line 812M from rice strain 8706, an indica/japonica hybrid, was grown in MS medium. One day after subculture the cells were transferred to Whatman filters for particle gun bombardment. Bombardments were performed with $CaCl_2$/spermidine precipitated plasmid DNA using a PDS-1000 as described for BMS cells (Example 3). The cells were allowed to express the introduced genes for two days and then harvested. β-Glucuronidase (GUS) and luciferase (LUX) were assayed as described, supra. As shown in Table 7, in duplicate experiments the presence of the HSP70 intron in the 5' untranslated region increases average GUS expression relative to LUX expression about 10 fold over the expression observed with the vector without an intron.

TABLE 7

Effect of HSP70 Intron in Rice

| Vector | Intron | GUS/LUX |
|---|---|---|
| pMON8677 | none | 15.5 |
| pMOM19433 | HSP70 | 150.7 |

EXAMPLE 15

Figure 27:
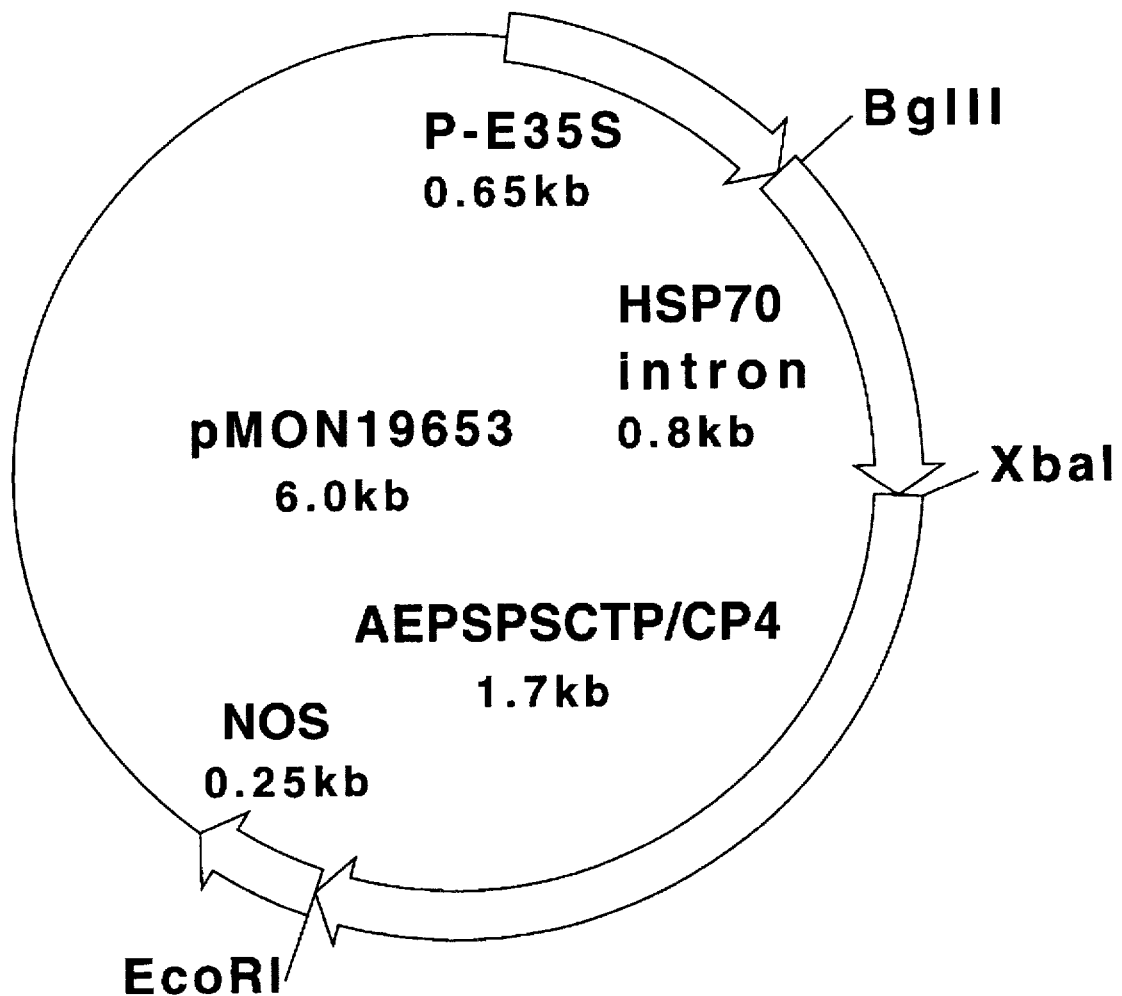
FIG. 27 illustrates a physical map of the plasmid pMON19653 comprising a CP4 coding sequence.

Expression of CP4 EPSPS using HSP70 intron vectors pMON19653 (FIG. 27) was constructed to test expression of the CP4 EPSPS gene (U.S. patent application Ser. No. 07/749,611 filed Aug. 28, 1991 incorporated herein by reference) in an HSP70 intron vector. A 1.7 kb BglII-EcoRI fragment containing the 300bp chloroplast transit peptide from the Arabidopsis EPSPS gene (AEPSPS CTP) fused in frame to the 1.4 kb bacterial CP4 EPSPS protein coding region was cloned into BamHI-EcoRI digested pMON19470 to form pMON19653. Thus, pMON19653 is comprised of, from 5' to 3', the enhanced CaMV35S promoter, HSP70 intron, AEPSPS CTP/CP4 coding sequence, and hopaline synthase polyadenylation region in a pUC-like backbone containing an NPTII gene for kanamycin selection in bacteria.

pMON19653 was introduced into embryogenic cells in combination with pMON19643 and transformed calli selected on glyphosate medium as described in Example 11. Glyphosate resistant embryogenic callus were assayed by Western Blot analysis. The amount of CP4 protein expressed was determined by comparison to standards of E. coli produced protein. Nine lines were generated. The CP4 expression levels ranged from undetectable to 0.3% of the total protein in crude extracts made from the embryogenic callus, with an average value of 0.17%.

The above examples indicate that the use of vectors containing the HSP70 intron would be expected to enhance the expression in monocot plants of other DNA sequences encoding proteins.

We claim:

1. In a method for the expression of a chimeric plant gene in monocot plants, the improvement which comprises expressing a chimeric plant gene comprising an intron selected from the group consisting of SEQ ID NO:1, SEQ ID NO:2 and SEQ ID NO:3 in the non-translated leader 5' of the structural DNA sequence encoding a protein.

2. The method of claim 1 in which the intron is SEQ ID NO:1.

3. The method of claim 1 in which the intron is SEQ ID NO:2.

4. The method of claim 1 in which the intron is SEQ ID NO:3.

5. The method of claim 2 in which the structural DNA sequence encodes a EPSP synthase.

6. The method of claim 2 in which the structural DNA sequence encodes ACC-deaminase.

7. The method of claim 2 in which the structural DNA sequence encodes a GOX protein.

8. The method of claim 2 in which the structural DNA sequence encodes a B.t. crystal toxin protein.

9. The method of claim 3 in which the structural DNA sequence encodes a glgC16 protein.

10. A transgenic monocot plant comprising a DNA construct comprising in sequence:
    (a) a promoter that functions in plant cells to cause the production of an RNA sequence;
    (b) a non-translated leader comprising an intron sequence selected from the group consisting of SEQ ID NO:1, SEQ ID NO:2, and SEQ ID NO:3;
    (c) a structural DNA sequence that causes the production of an RNA sequence that encodes a protein; and
    (d) a 3' nontranslated sequence that functions in plant cells to cause the addition of polyadenylated nucleotides to the 3' end of the RNA sequence; the intron being heterologous with respect to the promoter.

11. The plant of claim 10 in which the intron is the sequence of SEQ ID NO:1.

12. The plant of claim 10 in which the intron is the sequence of SEQ ID NO:2.

13. The plant of claim 10 in which the intron is the sequence of SEQ ID NO:3.

14. The plant of claim 11 in which the plant is maize.

15. The plant of claim 11 in which the plant is wheat.

16. The plant of claim 11 in which the plant is rice.

17. The plant of claim 11 in which the promoter is selected from the group consisting of a CaMV35S promoter and a FMV promoter.

18. The plant of claim 17 wherein the structural DNA sequence encodes for an EPSP synthase.

19. The plant of claim 11 wherein the structural DNA sequence encodes for a CP4 protein.

20. The plant of claim 11 wherein the structural DNA sequence encodes for ACC-deaminase.

21. The plant of claim 11 wherein the structural DNA sequence encodes for a B.t. crystal toxin protein.

22. The plant of claim 17 wherein the structual DNA sequence encodes for glgC16 protein.

23. The plant of claim 11 wherein the structual DNA sequence encodes for a plant viral coat protein.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 816 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
AGATCTACCG   TCTTCGGTAC   GCGCTCACTC   CGCCCTCTGC   CTTTGTTACT   GCCACGTTTC       60
TCTGAATGCT   CTCTTGTGTG   GTGATTGCTG   AGAGTGGTTT   AGCTGGATCT   AGAATTACAC      120
TCTGAAATCG   TGTTCTGCCT   GTGCTGATTA   CTTGCCGTCC   TTTGTAGCAG   CAAAATATAG      180
GGACATGGTA   GTACGAAACG   AAGATAGAAC   CTACACAGCA   ATACGAGAAA   TGTGTAATTT      240
GGTGCTTAGC   GGTATTTATT   TAAGCACATG   TTGGTGTTAT   AGGGCACTTG   GATTCAGAAG      300
TTTGCTGTTA   ATTTAGGCAC   AGGCTTCATA   CTACATGGGT   CAATAGTATA   GGGATTCATA      360
TTATAGGCGA   TACTATAATA   ATTTGTTCGT   CTGCAGAGCT   TATTATTTGC   CAAAATTAGA      420
TATTCCTATT   CTGTTTTTGT   TTGTGTGCTG   TTAAATTGTT   AACGCCTGAA   GGAATAAATA      480
TAAATGACGA   AATTTTGATG   TTTATCTCTG   CTCCTTTATT   GTGACCATAA   GTCAAGATCA      540
GATGCACTTG   TTTTAAATAT   TGTTGTCTGA   AGAAATAAGT   ACTGACAGTA   TTTTGATGCA      600
TTGATCTGCT   TGTTTGTTGT   AACAAAATTT   AAAAATAAAG   AGTTTCCTTT   TTGTTGCTCT      660
CCTTACCTCC   TGATGGTATC   TAGTATCTAC   CAACTGACAC   TATATTGCTT   CTCTTTACAT      720
ACGTATCTTG   CTCGATGCCT   TCTCCCTAGT   GTTGACCAGT   GTTACTCACA   TAGTCTTTGC      780
TCATTTCATT   GTAATGCAGA   TACCAAGCGG   CCATGG                                    816
```

( 2 ) INFORMATION FOR SEQ ID NO:2:

( i ) SEQUENCE CHARACTERISTICS:
        ( A ) LENGTH: 283 base pairs (B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:2:

```
AGATCTACCG TCTTCGGTAC GCGCTCACTC CGCCCTCTGC CTTTGTTACT GCCACGTTTC      60
TCTGAATGTG ATCTGCTTGT TTGTTGTAAC AAAATTTAAA AATAAAGAGT TTCCTTTTTG     120
TTGCTCTCCT TACCTCCTGA TGGTATCTAG TATCTACCAA CTGACACTAT ATTGCTTCTC     180
TTTACATACG TATCTTGCTC GATGCCTTCT CCCTAGTGTT GACCAGTGTT ACTCACATAG     240
TCTTTGCTCA TTTCATTGTA ATGCAGATAC CAAGCGGCCA TGG                       283
```

( 2 ) INFORMATION FOR SEQ ID NO:3:

(i) SEQUENCE CHARACTERISTICS:
    (A) LENGTH: 162 base pairs
    (B) TYPE: nucleic acid
    (C) STRANDEDNESS: single
    (D) TOPOLOGY: linear ( i i ) MOLECULE TYPE: DNA (genomic)

( x i ) SEQUENCE DESCRIPTION: SEQ ID NO:3:

```
AGATCTACCG TCTTCGGTAC GCGCTCACTC CGCCCTCTGC CTTTGTTACT GCCACGTTTC      60
TCTGAATGGT ATCTTGCTCG ATGCCTTCTC CCTAGTGTTG ACCAGTGTTA CTCACATAGT     120
CTTTGCTCAT TTCATTGTAA TGCAGATACC AAGCGGCCAT GG                        162
```